US008670523B2

(12) United States Patent
Yan et al.

(10) Patent No.: US 8,670,523 B2
(45) Date of Patent: Mar. 11, 2014

(54) INTENSITY MODULATED ARC THERAPY WITH CONTINUOUS COUCH ROTATION/SHIFT AND SIMULTANEOUS CONE BEAM IMAGING

(75) Inventors: Di Yan, Auburn Hills, MI (US); Alvaro Martinez, Bloomfield Hills, MI (US)

(73) Assignee: William Beaumont Hospital, Royal Oak, MI (US)

(*) Notice: Subject to any disclaimer, the term of this patent is extended or adjusted under 35 U.S.C. 154(b) by 302 days.

(21) Appl. No.: 12/930,348

(22) Filed: Jan. 4, 2011

(65) Prior Publication Data
US 2012/0020449 A1 Jan. 26, 2012

Related U.S. Application Data

(60) Provisional application No. 61/335,314, filed on Jan. 5, 2010.

(51) Int. Cl.
- A61B 6/04 (2006.01)
- A61B 6/00 (2006.01)
- A61N 5/10 (2006.01)
- H05G 1/02 (2006.01)

(52) U.S. Cl.
USPC ............................ 378/65; 378/20; 378/209

(58) Field of Classification Search
USPC ........... 378/4–20, 65, 91, 204, 205, 208–210; 5/600, 601, 81.1 RP, 607, 608; 600/425–429; 250/491.1
See application file for complete search history.

(56) References Cited

U.S. PATENT DOCUMENTS

| | | |
|---|---|---|
| 3,778,614 A | 12/1973 | Hounsfield |
| 3,780,291 A | 12/1973 | Stein et al. |
| 4,132,895 A | 1/1979 | Froggatt |
| 4,145,613 A | 3/1979 | Bunch |
| 4,304,999 A | 12/1981 | Richey et al. |
| 4,315,157 A | 2/1982 | Barnes |
| 4,380,818 A | 4/1983 | Pfeiler |
| 4,389,569 A | 6/1983 | Hattori et al. |
| 4,405,745 A | 9/1983 | Mathis et al. |
| 4,414,682 A | 11/1983 | Annis et al. |
| 4,534,051 A | 8/1985 | Grady et al. |

(Continued)

FOREIGN PATENT DOCUMENTS

| | | |
|---|---|---|
| CN | 1419891 A1 | 5/2003 |
| CN | 1748217 A1 | 3/2006 |

(Continued)

OTHER PUBLICATIONS

Vicini, F., et al., "NSABP B-39/RTOG 0413: A randomized phase III study of conventional whole breast irradiation versus partial breast irradiation for women with Stage 0, I, or II breast cancer," [Version Mar. 13, 2007.] Available from: http://rtog.org/members/protocols/0413/0413.pdf, publicly available as of Nov. 23, 2009, pp. 1-122.

(Continued)

*Primary Examiner* — Anastasia Midkiff
(74) *Attorney, Agent, or Firm* — Honigman Miller Schwartz and Cohn LLP; Douglas H. Siegel; Jonathan P. O'Brien

(57) ABSTRACT

A system for radiotherapy that includes a couch upon which a patient being treated by the system is positioned, the couch having continuous arc rotation for delivery accelerated irradiation to the patient.

38 Claims, 10 Drawing Sheets

(56) References Cited

U.S. PATENT DOCUMENTS

| | | | |
|---|---|---|---|
| 4,547,892 A | 10/1985 | Richey et al. | |
| 4,712,226 A | 12/1987 | Horbaschek | |
| 4,920,552 A | 4/1990 | Hermens | |
| 5,039,867 A | 8/1991 | Nishihara et al. | |
| 5,125,012 A | 6/1992 | Schittenheim | |
| 5,157,707 A | 10/1992 | Ohlson | |
| 5,214,686 A | 5/1993 | Webber | |
| 5,335,255 A | 8/1994 | Seppi et al. | |
| 5,379,333 A | 1/1995 | Toth | |
| 5,394,452 A | 2/1995 | Swerdloff et al. | |
| 5,411,026 A | 5/1995 | Carol | |
| 5,485,494 A | 1/1996 | Williams et al. | |
| 5,521,957 A | 5/1996 | Hansen | |
| 5,533,082 A | 7/1996 | Gronemeyer | |
| 5,602,892 A | 2/1997 | Llacer | |
| 5,625,661 A | 4/1997 | Oikawa | |
| 5,657,364 A | 8/1997 | Pfoh | |
| 5,661,773 A | 8/1997 | Swerdloff et al. | |
| 5,663,995 A | 9/1997 | Hu | |
| 5,675,625 A | 10/1997 | Rockseisen | |
| 5,699,805 A | 12/1997 | Seward et al. | |
| 5,719,914 A | 2/1998 | Rand et al. | |
| 5,724,400 A | 3/1998 | Swerdloff et al. | |
| 5,748,700 A | 5/1998 | Shepherd et al. | |
| 5,751,781 A | 5/1998 | Brown et al. | |
| 5,835,558 A | 11/1998 | Maschke | |
| 5,848,126 A | 12/1998 | Fujita et al. | |
| 5,864,597 A | 1/1999 | Kobayashi | |
| 5,877,501 A | 3/1999 | Ivan et al. | |
| 5,912,943 A | 6/1999 | Deucher et al. | |
| 5,929,449 A | 7/1999 | Huang | |
| 5,949,811 A | 9/1999 | Baba et al. | |
| 5,966,422 A | 10/1999 | Dafni et al. | |
| 5,999,587 A | 12/1999 | Ning et al. | |
| 6,031,888 A | 2/2000 | Ivan et al. | |
| 6,041,097 A | 3/2000 | Roos et al. | |
| 6,113,264 A | 9/2000 | Watanabe | |
| 6,148,058 A | 11/2000 | Dobbs | |
| 6,152,598 A | 11/2000 | Tomisaki et al. | |
| 6,200,024 B1 | 3/2001 | Negrelli | |
| 6,229,870 B1 | 5/2001 | Morgan | |
| 6,239,439 B1 | 5/2001 | Itabashi et al. | |
| 6,256,370 B1 | 7/2001 | Yavuz | |
| 6,259,766 B1 | 7/2001 | Cuppen | |
| 6,269,143 B1 | 7/2001 | Tachibana | |
| 6,285,739 B1 | 9/2001 | Rudin et al. | |
| 6,292,534 B1 | 9/2001 | Linders et al. | |
| 6,307,914 B1 | 10/2001 | Kunieda et al. | |
| 6,318,892 B1 | 11/2001 | Suzuki et al. | |
| 6,325,537 B1 | 12/2001 | Watanabe | |
| 6,345,114 B1 | 2/2002 | Mackie et al. | |
| 6,385,286 B1 | 5/2002 | Fitchard et al. | |
| 6,385,288 B1 | 5/2002 | Kanematsu | |
| 6,389,104 B1 | 5/2002 | Bani-Hashemi et al. | |
| 6,393,096 B1 | 5/2002 | Carol et al. | |
| 6,435,715 B1 | 8/2002 | Betz et al. | |
| 6,463,122 B1 | 10/2002 | Moore | |
| 6,546,073 B1 | 4/2003 | Lee | |
| 6,560,311 B1 | 5/2003 | Shepart et al. | |
| 6,582,121 B2 | 6/2003 | Crain et al. | |
| 6,618,466 B1 | 9/2003 | Ning | |
| 6,628,745 B1 | 9/2003 | Annis et al. | |
| 6,633,627 B2 | 10/2003 | Horiuchi | |
| 6,661,870 B2 | 12/2003 | Kapatoes et al. | |
| 6,707,876 B2 | 3/2004 | Tanigawa | |
| 6,760,402 B2 | 7/2004 | Ghelmansarai | |
| 6,792,074 B2 | 9/2004 | Erbel et al. | |
| 6,842,502 B2 | 1/2005 | Jaffray et al. | |
| 6,865,254 B2 | 3/2005 | Nafstadius | |
| 6,888,919 B2 | 5/2005 | Graf | |
| 6,907,100 B2 | 6/2005 | Taguchi | |
| 6,915,005 B1 | 7/2005 | Ruchala et al. | |
| 6,980,627 B2 | 12/2005 | Qiu et al. | |
| 6,990,175 B2 | 1/2006 | Nakashima et al. | |
| 6,993,112 B2 | 1/2006 | Hesse | |
| 7,030,386 B2 | 4/2006 | Pang et al. | |
| 7,062,006 B1 | 6/2006 | Pelc et al. | |
| 7,072,436 B2 | 7/2006 | Pelc | |
| 7,127,035 B2 | 10/2006 | Anno et al. | |
| 7,145,981 B2 | 12/2006 | Pelc | |
| 7,154,991 B2 * | 12/2006 | Earnst et al. | 378/65 |
| 7,170,975 B2 | 1/2007 | Distler et al. | |
| 7,193,227 B2 * | 3/2007 | Hiramoto et al. | 250/492.3 |
| 7,227,923 B2 | 6/2007 | Edic et al. | |
| 7,227,925 B1 | 6/2007 | Mansfield et al. | |
| 7,280,631 B2 | 10/2007 | De Man et al. | |
| 7,305,063 B2 | 12/2007 | Heuscher | |
| 7,388,940 B1 | 6/2008 | De Man et al. | |
| 7,428,292 B2 | 9/2008 | DeMan et al. | |
| 7,471,765 B2 | 12/2008 | Jaffray et al. | |
| 7,496,181 B2 | 2/2009 | Mazin et al. | |
| 7,657,304 B2 | 2/2010 | Mansfield et al. | |
| 7,760,849 B2 | 7/2010 | Zhang | |
| 7,826,592 B2 | 11/2010 | Jaffray et al. | |
| 7,945,021 B2 | 5/2011 | Shapiro et al. | |
| 8,073,104 B2 | 12/2011 | Yan et al. | |
| 2003/0072407 A1 | 4/2003 | Mihara et al. | |
| 2003/0095627 A1 | 5/2003 | Anderton | |
| 2003/0138077 A1 | 7/2003 | Lee | |
| 2003/0191363 A1 | 10/2003 | Boll et al. | |
| 2003/0235271 A1 | 12/2003 | Rand | |
| 2004/0002641 A1 | 1/2004 | Sjogren et al. | |
| 2004/0081270 A1 | 4/2004 | Heuscher | |
| 2004/0086074 A1 | 5/2004 | Taguchi | |
| 2004/0096033 A1 | 5/2004 | Seppi et al. | |
| 2004/0120452 A1 | 6/2004 | Shapiro et al. | |
| 2004/0174949 A1 | 9/2004 | Yamashita et al. | |
| 2004/0254448 A1 | 12/2004 | Amies et al. | |
| 2005/0013404 A1 | 1/2005 | Kasperl et al. | |
| 2005/0027196 A1 | 2/2005 | Fitzgerald | |
| 2005/0054937 A1 | 3/2005 | Takaoka et al. | |
| 2005/0058237 A1 | 3/2005 | Morf | |
| 2005/0080336 A1 | 4/2005 | Byrd et al. | |
| 2005/0085710 A1 | 4/2005 | Earnst et al. | |
| 2005/0111610 A1 | 5/2005 | DeMan et al. | |
| 2005/0111616 A1 | 5/2005 | Li et al. | |
| 2005/0111621 A1 | 5/2005 | Riker et al. | |
| 2005/0197564 A1 | 9/2005 | Dempsey | |
| 2005/0234327 A1 * | 10/2005 | Saracen et al. | 600/407 |
| 2005/0249432 A1 | 11/2005 | Zou et al. | |
| 2005/0251029 A1 | 11/2005 | Khamene et al. | |
| 2006/0002506 A1 | 1/2006 | Pelc | |
| 2006/0008047 A1 | 1/2006 | Zhou et al. | |
| 2006/0017009 A1 | 1/2006 | Rink et al. | |
| 2006/0239409 A1 | 10/2006 | Levene et al. | |
| 2006/0245543 A1 | 11/2006 | Earnst et al. | |
| 2006/0259282 A1 | 11/2006 | Failla et al. | |
| 2006/0269049 A1 | 11/2006 | Yin et al. | |
| 2006/0274885 A1 | 12/2006 | Wang et al. | |
| 2006/0285639 A1 | 12/2006 | Olivera et al. | |
| 2006/0285640 A1 | 12/2006 | Nizin et al. | |
| 2006/0285641 A1 | 12/2006 | Scherch | |
| 2007/0003123 A1 | 1/2007 | Fu et al. | |
| 2007/0016014 A1 | 1/2007 | Hara et al. | |
| 2007/0019782 A1 | 1/2007 | Van Stevendaal et al. | |
| 2007/0053492 A1 | 3/2007 | Kindani et al. | |
| 2007/0076846 A1 | 4/2007 | Ruchala et al. | |
| 2007/0280408 A1 | 12/2007 | Zhang | |
| 2008/0031406 A1 * | 2/2008 | Yan et al. | 378/14 |
| 2010/0119032 A1 | 5/2010 | Yan et al. | |
| 2010/0135454 A1 | 6/2010 | Noo | |
| 2011/0002439 A1 | 1/2011 | Zhang | |
| 2011/0080992 A1 | 4/2011 | Dafni | |
| 2011/0211666 A1 | 9/2011 | Ying et al. | |

FOREIGN PATENT DOCUMENTS

| | | |
|---|---|---|
| CN | 1758876 A1 | 4/2006 |
| DE | 1992708 U | 8/1968 |
| DE | 2822241 A1 | 12/1978 |
| EP | 0314231 A2 | 5/1989 |
| EP | 0922943 A2 | 6/1999 |
| JP | 5252594 A | 4/1977 |
| JP | 56101579 A | 8/1981 |

(56) References Cited

FOREIGN PATENT DOCUMENTS

| | | |
|---|---|---|
| JP | 56168578 A | 12/1981 |
| JP | 5894835 A | 6/1983 |
| JP | 4242736 A | 8/1992 |
| JP | 04307035 | 10/1992 |
| JP | 5172764 A | 7/1993 |
| JP | 06506860 | 8/1994 |
| JP | 07255717 A | 10/1995 |
| JP | 8122438 A | 5/1996 |
| JP | 9327453 A | 12/1997 |
| JP | 10113400 A | 5/1998 |
| JP | 10511595 A | 11/1998 |
| JP | 10328318 A | 12/1998 |
| JP | 11047290 A | 2/1999 |
| JP | 1199148 A | 4/1999 |
| JP | 11160440 A | 6/1999 |
| JP | 2000126164 A | 5/2000 |
| JP | 2000308634 A | 11/2000 |
| WO | WO97/13552 A1 | 4/1997 |
| WO | WO98/52635 | 11/1998 |
| WO | WO99/03397 | 1/1999 |
| WO | WO2004061744 A2 | 7/2004 |
| WO | WO2004080309 A2 | 9/2004 |
| WO | WO2006/018761 A1 | 2/2006 |
| WO | WO2007/120744 A2 | 10/2007 |

OTHER PUBLICATIONS

Hepel, Jaroslaw T., et al., "Toxicity of three-dimensional conformal radiotherapy for accelerated partial breast irradiation," Int. J. Radiat. Oncol. Biol. Phys., vol. 75, No. 5, 2009; pp. 1290-1296.
Jagsi, Reshma, et al., "Unacceptable cosmesis in a protocol investigating intensity-modulated radiotherapy with active breathing control for accelerated partial-breast irradiation," Int. J. Radiat. Oncol. Biol. Phys., vol. 76, No. 1, 2009, pp. 71-78.
Livi, Lorenzo, et al., "Accelerated partial breast irradiation with IMRT: new technical approach and interim analysis of acute toxicity in a phase III randomized clinical trial," Int. J. Radiat. Oncol. Biol. Phys., vol. 77, No. 2, Jun. 1, 2010, pp. 509-515.
Smith, Benjamin D., et al., "Accelerated partial breast irradiation consensus statement from the american society for radiation oncology (ASTRO)," Int. J. Radiat. Oncol. Biol. Phys., vol. 74, No. 4, 2009, pp. 987-1001.
Veronesi, Umberto, et al., "Twenty year follow-up of a randomized study comparing breast-conserving surgery with radical mastectomy for early breast cancer," N. Engl. J. Med., vol. 347, No. 16, Oct. 17, 2002, pp. 1227-1232.
Jain, Anudh K., et al., "Does three-dimensional external beam partial breast irradiation spare lung tissue compared with standard whole breast irradiation?" Int. J. Radiat. Oncol. Biol. Phys., vol. 75, No. 1, 2009, pp. 82-88.
Recht, Abram, et al., "Lung dose-volume parameters and the risk of pneumonitis for patients treated with accelerated partial-breast irradiation using three-dimensional conformal radiotherapy," J. Clin. Oncol., vol. 27, No. 24, Aug. 20, 2009, pp. 3887-3893.
Low, Jennifer A,, et al., "Long-term follow-up for locally advanced and inflammatory breast cancer patients treated with multimodality therapy," J. Clin. Oncol., vol. 22, No. 20, Oct. 15, 2004, pp. 4067-4074.
Romond, Edward H., et al., "Trastuzumab plus adjuvant chemotherapy for operable HER2-positive breast cancer," N. Engl. J. Med., vol. 353, No. 16, Oct. 20, 2005, pp. 1673-1684.
Piccart-Gebhart, Martine J., et al., "Trastuzumab after adjuvant chemotherapy in HER2-positive breast cancer," N. Engl. J. Med., vol. 353, No. 16, Oct. 20, 2005, pp. 1659-1672.
Berrington de Gonzalez, A., et al., "Second solid cancers after radiotherapy for breast cancer in SEER cancer registries," Br. J. Cancer 2009, vol. 102, No. 1, Jan. 5, 2010, pp. 220-226.
Stovall, Marilyn, et al., "Dose to the contralateral breast from radiotherapy and risk of second primary breast cancer in the WECARE study," Int. J. Radiat. Oncol. Biol. Phys., vol. 72, No. 4, 2008, pp. 1021-1030.
Kozak, Kevin R, et al., "Dosimetric comparison of two different three-dimensional conformal external beam accelerated partial breast irradiation techniques," Int. J. Radiat. Oncol. Biol. Phys., vol. 65, No. 2, 2006, pp. 340-346.
Rusthoven, Kyle E., et al., "Accelerated partial-breast intensity-modulated radiotherapy results in improved dose distribution when compared with three-dimensional treatment-planning techniques," Int. J. Radiat. Oncol. Biol. Phys., vol. 70, No. 1, 2008, pp. 296-302.
Moran, Jean M., et al., "Accelerated partial breast irradiation: what is dosimetric effect of advanced technology approaches?," Int. J. Radiat. Oncol. Biol. Phys., vol. 75, No. 1, 2009, pp. 294-301.
Wernicke, A.G., et al., "External beam partial breast irradiation following breast-conserving surgery: preliminary results of cosmetic outcome of NYU 00-23," Int. J. Radiat. Oncol. Biol. Phys. vol. 66, No. 3, Supplement, 2006, p. S32.
Formenti, Silvia C., et al., "Prone accelerated partial breast irradiation after breast-conserving surgery: preliminary clinical results and dose-volume histogram analysis," Int. J. Radiat. Oncol. Biol. Phys., vol. 60, No. 2, 2004, pp. 493-504.
Kozak, Kevin R., et al., "Dosimetric comparison of proton and photon three-dimensional, conformal, external beam accelerated partial breast irradiation techniques," Int. J. Radiat. Oncol. Biol. Phys., vol. 65, No. 5, 2006, pp. 1572-1578.
Yu CX., "Intensity-modulated arc therapy with dynamic multileaf collimation: an alternative to tomotherapy," Phys. Med. Biol., vol. 40, 1995, pp. 1435-1449.
Yu, Cedric X., et al., "Clinical implementation of intensity-modulated arc therapy," Int. J. Radiat. Oncol. Biol. Phys.. vol. 53, No. 2, 2002, pp. 453-463.
Otto K., "Volumetric modulated arc therapy: IMRT in a single gantry arc," Med. Phys., vol. 35, 2008, pp. 310-317.
Palma, David, et al., "Volumetric modulated arc therapy for delivery of prostate radiotherapy: comparison with intensity-modulated radiotherapy and three-dimensional conformal radiotherapy," Int. J. Radiat. Oncol. Biol. Phys., vol. 72, No. 4, 2008, pp. 996-1001.
Duthoy, W., et al., "Clinical implementation of intensity-modulated arc therapy (IMAT) for rectal cancer," Int. J. Radiat. Oncol. Biol. Phys., vol. 60, No. 3, 2004, pp. 794-806.
Lagerwaard FJ., et al., "Whole-brain radiotherapy with simultaneous integrated boost to multiple brain metastases using volumetric modulated arc therapy," Int. J. Radiat. Oncol. Biol. Phys., vol. 75, No. 1, 2009, pp. 253-259.
Popescu CC., et al., "Volumetric modulated arc therapy improves dosimetry and reduces treatment time compared to conventional intensity-modulated radiotherapy for locoregional radiotherapy of left-sided breast cancer and internal mammary nodes," Int J Radiat Oncol Biol Phys, vol. 76, No. 1, 2009, pp. 287-295.
Clarke M., et al., "Effects of radiotherapy and of differences in the extent of surgery for early breast cancer on local recurrence and 15-year survival: An overview of the randomised trials," Lancet, vol. 366, 2005, pp. 2087-2106.
Paszat, Lawrence F., et al., "Mortality from myocardial infarction following postlumpectomy radiotherapy for breast cancer: A population-based study in Ontario, Canada," Int J Radiat Oncol Biol Phys, vol. 43, No. 4, 1999, pp. 755-762.
Baglan, Kathy L. et al., "Accelerated partial breast irradiation using 3D conformal radiation therapy (3D-CRT)," Int J Radiat Oncol Biol Phys, vol. 55, No. 2, 2003, pp. 302-311.
Pignol, Jean-Philippe, et al., "A multicenter randomized trial of breast intensity-modulated radiation therapy to reduce acute radiation dermatitis," J Clin Oncol, vol. 26, No. 13, May 1, 2008, pp. 2085-2092.
Reeder, Reed, et al., "Predictors for clinical outcomes after accelerated partial breast intensity-modulated radiotherapy," Int J Radiat Oncol Biol Phys, vol. 74. No. 1, 2009, pp. 92-97.
Hall, Eric J., et al., "Radiation-induced second cancers: The impact of 3D-CRT and IMRT," Int J Radiat Oncol Biol Phys, vol. 56, No. 1, 2003, pp. 83-88.
Shaitelman, Simona F., et al., "Continuous Arc Rotation of the Couch Therapy for the Delivery of Accelerated Partial Breast Irradiation: A Treatment Planning Analysis," Int. J. Radiation Oncology Biol. Phys., vol. 80, No. 3, 2011, pp. 771-778.

(56) References Cited

OTHER PUBLICATIONS

Takahashi, S., "Conformation Radiotherapy. Rotation Techniques as Applied to Radiography and Radiotherapy of Cancer," Acta Radiol, Diagn (Stockh), Suppl 242:1+, 1965, pp. 11-140.

Kim, L., et al., "Volumetric Modulated Arc Therapy Using a Rotating Couch: An Accelerated Partial Breast Irradiation Planning Study," Int. L. Radiation Oncology Biol. Phys., vol. 75, Issue 3, Supplement 1, Nov. 1, 2009, pp. S732-S733.

Burgess, L., et al., "Partial Brain VMAT Planning Using Simultaneous Couch and Gantry Arcs," Int. L. Radiation Oncology Biol. Phys., vol. 78, Issue 3, Supplement 1, Nov. 1, 2010, pp. S818-S819.

International Search Report and Written Opinion for International Application No. PCT/US2011/000006 mailed Mar. 1, 2011.

Antonuk, L.E., et al., "A Real-Time, Flat-Panel, Amorphous Silicon, Digital X-Ray Imager", Radiographics, vol. 15, No. 4, Jul. 1995, pp. 993-1000.

Antonuk, L.E., et al., "Initial Performance Evaluation of an Indirect-Detection, Active Matrix Flat-Panel Imager (AMFPI) Prototype for Megavoltage Imaging", Int. J. Radiat. Oncol. Biol. Phys., vol. 42, No. 2, 1998, pp. 437-454.

Antonuk, L.E., et al., "Megavoltage Imaging with a Large-Area, Flat-Panel, Amorphous Silicon Imager", Int. J. Radiat. Oncol. Biol. Phys., vol. 36, No. 3, 1996, pp. 661-672.

Antonuk, L.E., et al., "Strategies to Improve the Signal and Noise Performance of Active Matrix, Flat-Panel Imagers for Diagnostic X-Ray Applications", Med. Phys., vol. 27, No. 2, Feb. 2000, pp. 289-306.

Basset, P.G., Wong, J.W. and Aspin, N.: "An Interactive Computer System for Studying Human Mucociliary Clearance", Computer Biol. Med. 1979, vol. 9, pp. 97-105.

Birkner, M., et al., "Adapting Inverse Planning to Patient and Organ Geometrical Variation: Algorithm and Implementation," Med. Phys., vol. 30, No. 10, Oct. 2003, pp. 2822-2831.

Bissonnette, J.P., et al., "Optimal Radiographic Magnification for Portal Imaging.", Med. Phys., vol. 21, No. 9, Sep. 1994, pp. 1435-1445.

Boyer, A.L., et al., "A Review of Electronic Portal Imaging Devices (EPIDs)", Medical Physics, Jan./Feb. 1992, vol. 19, No. 1, pp. 19: 1-16.

Boyer, A.L., et al., (IMRT Collaborative Working Group): "Intensity-modulated radiotherapy: Current status and issues of interest", Int. J. Radiat. Oncol. Biol. Phys. 2001, vol. 51, No. 4, pp. 880-914.

Brown, A.P., et al., "Three-Dimensional Photon Treatment Planning for Hodgkin's Disease", Int. J. Radiat. Oncol. Biol. Phys., May 15, 1991, vol. 21, No. 1, pp. 205-215.

Chen, J., et al., "Dose-Guided Radiation Therapy with Megavoltage Cone-Beam CT," published by The British Journal of Radiology, vol. 79, 2006, pp. S87-S98.

Cheng, A., et al., "Systematic Verification of a Three-Dimensional Electron Beam Dose Calculation Algorithm", Med. Phys., 1996, vol. 23, No. 5, pp. 685-693.

Chi, Y., et al., "A Material Sensitivity Study on the Accuracy of Deformable Organ Registration Using Linear Biomechanical Models," Med. Phys., vol. 33: No. 2, Feb. 2006, pp. 421-433.

Cullity, B.D., "Elements of X-Ray Diffraction, Second Edition," (Reading, MA: Addison Wesley, 1978), p. 6-12.

Dieu, L., et al., "Ion Beam Sputter-Deposited SiN/TiN Attenuating Phase-Shift Photoblanks," publication source and date unknown, 8 pages.

Drake, D.G., et al., "Characterization of Fluoroscopic Imaging System for kV and MV Radiography", Med. Phys., May 2000, vol. 27, No. 5, pp. 898-905.

Du, M.N., et al., "A Multileaf Collimator Field Prescription Preparation System for Conventional Radiotherapy", Int. J. Radiat. Oncol. Biol. Phys., 1994, vol. 30, No. 3, pp. 707-714.

Du, M.N., et al., "A Multileaf Collimator Field Prescription Preparation System for Conventional Radiotherapy", Int. J. Radiat. Oncol. Biol. Phys., 1995, vol. 32, No. 2, pp. 513-520.

El-Mohri, Y., et al., "Relative Dosimetry Using Active Matrix Flat-Panel Imager (AMFPI) Technology", Med. Phys., Aug. 1999, vol. 26, No. 8, pp. 1530-1541.

European Search Report for Application No. 07755309.7, dated Apr. 15, 2011, ten pages.

Ezz, A., et al., "Daily Monitoring and Correction of Radiation Field Placement Using a Video-Based Portal Imaging System: a Pilot Study", Int. J. Radiat. Oncol. Biol. Phys., 1992, vol. 22, No. 1, pp. 159-165.

Frazier, A., et al., "Dosimetric Evaluation of the Conformation of the Multileaf Collimator to Irregularly Shaped Fields", Int. J. Radiat. Oncol.Biol. Phys., 1995, vol. 33, No. 5, pp. 1229-1238.

Frazier, A., et al., "Effects of Treatment Setup Variation on Beam's Eye View Dosimetry for Radiation Therapy Using the Multileaf Collimator vs. the Cerrobend Block", Int. J. Radiat. Oncol. Biol. Phys., 1995, vol. 33, No. 5, pp. 1247-1256.

Ghilezan, M., et al., "Online Image-Guided Intensity-Modulated Radiotherapy for Prostate Cancer. How Much Improvement Can We Expect? A Theoretical Assessment of Clinical Benefits and Potential Dose Escalation by Improving Precision and Accuracy of Radiation Delivery," Int. J. Radiation Oncology Biol. Phys., vol. 60, No. 5, 2004, pp. 1602-1610.

Graham, M.L., et al., "A Method to Analyze 2-Dimensional Daily Radiotherapy Portal Images from an On-Line Fiber-Optic Imaging System.", Int. J. Radiat. Oncol. Biol. Phys., Mar. 1991, vol. 20, No. 3, pp. 613-619.

Gupta, N.K., et al., "Tangential CT, A Computed Tomography Method Developed for Industrial Inspection," 16th WCNDT 2004, Sep. 2004, five pages.

Halverson, K.J., et al., "Study of Treatment Variation in the Radiotherapy of Head and Neck Tumors Using a Fiber-Optic On-Line Line Radiotherapy Imaging System", Int. J. Radiat. Oncol. Biol. Phys., Oct. 1991, vol. 21, No. 5, pp. 1327-1336.

Harms, W.B., Sr., et al., "A Software Tool for the Quantitative Evaluation of 3D Dose Calculation Algorithms", Med. Phys., Oct. 1998, vol. 25, No. 10, pp. 1830-1839.

Herman, M.G., et al. "Clinical use of electronic portal imaging: Report of AAPM Radiation Therapy Committee Task Group 58", Med. Phys. May 2001, vol. 28, No. 5, pp. 712-737.

Jaffray, D.A., et al., "A Radiographic and Tomographic Imaging System Integrated into a Medical Linear Accelerator for Localization of Bone and Soft-Tissue Targets", Int. J. Radiat. Oncol. Biol. Phys., 1999, vol. 45, No. 3, pp. 773-789.

Jaffray, D.A., et al., "Activity Distribution of a Cobalt-60 Teletherapy Source", Med. Phys., Mar./Apr. 1991, vol. 18, No. 2, pp. 288-291.

Jaffray, D.A., et al., "Cone-Beam Computed Tomography with a Flat-Panel Imager: Initial Performance Characterization", Med. Phys. Jun. 2000, vol. 27, No. 6, pp. 1311-1323.

Jaffray, D.A., et al., "Dual-Beam Imaging for Online Verification of Radiotherapy Field Placement", Int. J. Radiat. Oncol. Biol. Phys., 1995, vol. 33, No. 5, pp. 1273-1280.

Jaffray, D.A., et al., "X-Ray Scatter in Megavoltage Transmission Radiography: Physical Characteristics and Influence on Image Quality", Med. Phys., Jan. 1994, vol. 21, No. 1, pp. 45-60.

Jaffray, D.A., et al., "X-Ray Sources of Medical Linear Accelerators: Focal and Extra-Focal Radiation", Med. Phys. Sep./Oct. 1993, vol. 20, No. 5, pp. 1417-1427.

Jaffray, et al., "Cone-Beam Computed Tomography with a Flat-Panel Imager: Initial Performance Characterization," Submission to the Medical Physics Journal for publication on Aug. 1999, 36 pages.

Jaffray, et al., Cone-Beam CT: Applications in Image-Guided External Beam Radiotherapy and Brachytherapy, publication source unknown, date unknown, one page.

Jaffray, et al., "Conebeam Tomographic Guidance of Radiation Field Placement for Radiotherapy of the Prostate," Manuscript accepted for publication in the International Journal of Radiation Oncology, Biology, Oct. 1998, 32 pages.

Jaffray, et al., "Exploring 'Target of the Day' Strategies for a Medical Linear Accelerator with Conebeam-CT Scanning Capability," XIIth ICCR held in Salt Lake City, Utah, May 27-30, 1997, pp. 172-174.

Jaffray, et al., "Flat-Panel Cone-Beam CT for Image-Guided External Beam Radiotherapy," publication source unknown, Oct. 1999, 36 pages.

(56) References Cited

OTHER PUBLICATIONS

Jaffray, et al., "Managing Geometric Uncertainty in Conformal Intensity-Modulated Radiation Therapy," Seminars in Radiation Oncology, vol. 9, No. 1, Jan. 1999 pp. 4-19.

Jaffray, et al., "Performance of a Volumetric CT Scanner Based Upon a Flat-Panel Imager," SPIE Physics of Medical Imaging, vol. 3659, Feb. 1999, pp. 204-214.

Kapatoes, J.M., et al., "On the Accuracy and Effectiveness of Dose Reconstruction for Tomotherapy," Phys. Med. Biol., vol. 46, 2001, pp. 943-966.

Kessler, M.L., "Image Registration and Data Fusion in Radiation Therapy," The British Journal of Radiology, vol. 79, 2006, pp. S99-S108.

Kestin, L.L., et al., "Improving the Dosimetric Coverage of Interstitial High-Dose-Rate Breast Implants", Int. J. Radiat. Oncol. Biol. Phys., 2000, vol. 46, No. 1, pp. 35-43.

Kestin, L.L., et al., "Intensity Modulation to Improve Dose Uniformity with Tangential Breast Radiotherapy: Initial Clinical Experience" Int J. Radiat, Oncol. Biol. Phys., 2000, vol. 48, No. 5, pp. 1559-1568.

Kini, V.R., et al., "Use of Three-Dimensional Radiation Therapy Planning Tools and Intraoperative Ultrasound to Evaluate High Dose Rate Prostate Brachytherapy Implants", Int. J. Radiat. Oncol. Biol. Phys., 1999, vol. 43, No. 3, pp. 571-578.

Kress, J., et al. "Patient position verification using CT images" Medical Physics, AIP, 26(6) 1999, 941-948.

Laughlin, J.S., et al., (writing chairs), "Evaluation of High Energy Photon External Beam Treatment Planning: Project Summary", Int. J. Rad. Oncol. Biol. Physics. 1991, vol. 21, pp. 3-8.

Liang, J., et al., "Reducing Uncertainties in Volumetric Image Based Deformable Organ Registration," Med. Phys., vol. 30, No. 8, Aug. 2003, pp. 2116-2122.

Lockman, D., et al., "Estimating the Dose Variation in a Volume of Interest with Explicit Consideration of Patient Geometric Variation," Med. Phys., vol. 27, No. 9, Sep. 2000, pp. 2100-2108.

Lucas, "Analysis of surface dose variation in CT procedures." The British Journal of Radiology, 74 (2001), 1128-1136.

Martinez, A., et al., "Improvement in dose escalation using the process of adaptive radiation therapy combined with three dimensional conformal or Intensity modulated beams for prostate cancer", Int. J. Radiat. Oncol. Biol. Phys. 2001, vol. 50, No. 5, pp. 1226-1234.

Masterson, M.E., et al., "Inter-Institutional Experience in Verification of External Photon Dose Calculations", Int. J. Rad. Oncol. Biol. Physics, 1991, vol. 21, pp. 37-58.

Michalski, J., et al., "An Evaluation of Two Methods of Anatomical Alignment of Radiotherapy Portal Images", Int. J. Radiat. Oncol. Biol. Phys., 1993; vol. 27. No. 5, pp. 1199-1206.

Michalski, J.M., et al., "Prospective Clinical Evaluation of an Electronic Portal Imaging Device", Int. J. Radiat. Oncol. Biol. Phys., 1996, vol. 34, No. 4, pp. 943-951.

Michalski, J.M., et al., "The Use of On-Line Image Verification to Estimate the Variation in Radiation Therapy Dose Delivery", Int. J. Radiat. Oncol. Biol. Phys., 1993, vol. 27, No. 3, pp. 707-716.

Milliken, B.D., et al., "Verification of the Omni Wedge Technique", Med. Phys. Aug. 1998, vol. 25, No. 8, pp. 1419-1423.

Mohan, R. (writing chair), "Three-Dimensional Dose Calculations for Radiation Treatment Planning", Int. J. Rad. Oncol. Biol. Physics, May 15, 1991; vol. 21, No. 1, pp. 25-36.

Mueller, K., et al., "Cone-Beam Computed Tomography (CT) for a Megavoltage Linear Accelerator (LINAC) Using an Electronic Portal Imaging Device (EPID) and the Algebraic Reconstruction Technique (ART)," publication on source unknown, (publication date unknown), 4 pages, while the date of publication is unknown, it is believe that the article was publicly available before May 24, 2007.

Nakagawa, K. et al., "development of a megavoltage ct scanner using linear accelerator treatment beam", Journal of Jastro, vol. 3, No. 4, pp. 265-276, 1991, Japanese Society for Therapeutic Radiology and Oncology.

Oldham, M., et al., "Practical aspects of in situ 160(y,n)150 activation using a conventional medical accelerator for the purpose of perfusion imaging", Med. Phys. Aug. 2001; vol. 28, No. 8, pp. 1669-1678.

Perera, H., et al., "Rapid Two-Dimensional Dose measurement in Brachytherapy Using Plastic Scintillator Sheet: Linearity, Signal-to-Noise Ratio, and Energy Response Characteristics.", Int. J. Radiat. Oncol. Biol. Phys., 1992, vol. 23, No. 5, pp. 1059-1069.

Pisani, L., et al., "Setup Error in Radiotherapy: On-line Correction Using Electronic Kilovoltage and Megavoltage Radiographs", Int. J. Radiat. Oncol. Biol. Phys., 2000, vol. 47, No. 3, pp. 825-839.

Purdy, J.A., et al., "State of the Art High Energy Photon Treatment Planning", Front Radiat. Ther. Oncol., 1987, vol. 21, pp. 4-24.

Schaly, B., et al., "Tracking the Dose Distribution in Radiation Therapy by Accounting for Variable Anatomy," Phys. Med. Biol., vol. 49, 2004, pp. 791-805.

Schmidt, T.G., et al., "A Prototype Table-Top Inverse-Geometry Volumetric CT Images," Med. Phys., vol. 33, No. 6, 2006, pp. 1867-1878.

Sharpe, M.B., et al., "Compensation of X-Ray Beam Penumbra in Conformal Radiotherapy", Med. Phys., Aug. 2000, vol. 27, No. 8, pp. 1739-1745.

Sharpe, M.B., et al., "Monitor Unit Settings for Intensity Modulated Beams Delivered Using a Step-and-Shoot Approach", Med. Phys., Dec. 2000, vol. 27, No. 12, pp. 2719-2725.

Shikhaliev, P.M., et al., "Photon Counting Computed Tomography: Concept and Initial Results," Med. Phys., vol. 32, No. 2, 2005, abstract.

Shirato, H., "real-time tumor tracking radiotherapy and stereotactic irradiation", Monthly New Medical Care, vol. 26, No. 12, pp. 61-63, 1999, ME Co., Ltd.

Shiu, A.S., et al., "Verification Data for Electron Beam Dose Algorithms", Med. Phys., May/Jun. 1992, vol. 19, No. 3, pp. 623-636.

Siewerdsen, et al., "Cone-Beam Computed Tomography with a Flat-Panel Imager: Effects of Image Lag," Med. Phys., vol. 26, No. 12, Dec. 1999, pp. 2635-2647.

Siewerdsen, et al., "Cone-Beam CT with a Flat-Panel Imager: Noise Consideration for Fully 3-D Computed Tomography," SPIE Physics of Medical Imaging, vol. 3336, Feb. 2000, pp. 546-554.

Siewerdsen, et al., "Optimization of X-Ray Imaging Geometry (with Specific Application to Flat-Panel Cone-Beam Computed Tomography)," Non-Final Version of Manuscript to be published in Med. Phys., vol. 27, No. 8, Aug. 2000, pp. 1-12.

Siewerdsen, J.H., et al., "A Ghost Story: Spatio-Temporal Response Characteristics of an Indirect-Detection Flat-Panel Imager", Med. Phys., Aug. 1999, vol. 26, No. 8, pp. 1624-1641.

Siewerdsen, J.H., et al., "Cone-Beam Computed Tomography with a Flat-Panel Imager: Magnitude and Effects of X-Ray Scatter", Med. Phys., Feb. 2001, vol. 28, No. 2, pp. 220-231.

Siewerdsen, J.H., et al., "Empirical and Theoretical Investigation of the Noise Performance of Indirect Detection, Active Matrix Flat-Panel Imagers (AMFPIs) for Diagnostic Radiology", Med. Phys., Jan. 1997, vol. 24, No. 1, pp. 71-89.

Siewerdsen, J.H., et al., "Optimization of X-Ray Imaging Geometry (with Specific Application to Flat-Panel Cone-Beam Computed Tomography)", Med. Phys., Aug. 2000, vol. 27, No. 8, pp. 1903-1914.

Siewerdsen, JH, et al., "Signal, Noise Power Spectrum, and Detective Quantum Efficiency of Indirect-Detection Flat-Panel Panel Imagers for Diagnostic Radiology", Med. Phys., May 1998, vol. 25, No. 5, pp. 614-628.

Sohn, M. et al., "Modeling Individual Geometric Variation Based on Dominant Eigenmodes of Organ Deformation: Implementation and Evaluation," Phys Med Biol, vol. 50, 2005, pp. 5893-5908.

Sontag, M.R. and Purdy, J.A. (writing chairs), "State of the Art of External Photon Beam Radiation Treatment Planning", Int. J. Rad. Oncol. Biol. Physics. 1991, vol. 21 No. 1, pp. 9-23.

Stromberg, J.S., et al., "Active Breathing Control (ABC) for Hodgkin's Disease: Reduction in Normal Tissue Irradiation with Deep Inspiration and Implications for Treatment", Int. J. Radiat. Oncol. Biol. Phys. 2000, vol. 48, No. 3, pp. 797-806.

Teicher, B.A., et al., "Allosteric Effectors of Hemoglobin as Modulators of Chemotherapy and Radiation Therapy In Vitro and In Vivo", Cancer Chemother. Pharmacol., 1998, vol. 42, pp. 24-30.

(56) References Cited

OTHER PUBLICATIONS

Tepper, J.E. and Shank, B. (writing Chairs), "Three-Dimensional Display in Planning Radiation Therapy: A Clinical Perspective", Int. J. Rad. Oncol. Biol. Physics. 1991, vol. 21, No. 1, pp. 79-89.

Urie, M.M., et al., "The Role of Uncertainty Analysis in Treatment Planning", Int. J. Radiat. Oncol. Biol. Phys., 1991, vol. 21, No. 1, pp. 91-107.

Vicini, F.A., et al., "Dose-vol. Analysis for Quality Assurance of Interstitial Brachytherapy for Breast Cancer", Int. J. Radiat. Oncol. Biol. Phys., 1999, vol. 45, No. 3, pp. 803-810.

Vicini, F.A., et al., "Implementation of a 3D-Virtual Brachytherapy in the Management of Breast Cancer a Description of a New Method of Interstitital Brachytherapy", Int. J. Radiat. Oncol. Biol. Phys., 1998, vol. 40, No. 3, pp. 629-635.

Vicini, F.A., et al., "Low-Dose-Rate Brachytherapy as the Sole Radiation Modality in the Management of Patients with Early-Stage Breast Cancer Treated with Breast-Conceiving Therapy: Preliminary Results of a Pilot Trial", Int. J. Radiat. Oncol. Biol. Phys., 1997, vol. 38, No. 2, pp. 301-310.

Webb, S., et al., Abstract of "Monte Carlo Modelling of the Performance of a Rotating Slit-collimator for Improved Planar Gamma-Camera Imaging," Phys. Med. Biol., vol. 37, No. 5, 1992, abstract.

Weinberg, R., et al., "Dosimetric Uncertainties of Three-Dimensional Dose Reconstruction from Two-Dimensional Data in a Multi-Institutional Study," Journal of Applied Clinical Medical Physics, vol. 5, No. 4, Fall 2004, pp. 15-28.

Williamson, J.F., et al., "One-Dimensional Scatter-Subtraction Method for Brachytherapy Calculation Near Bounded Heterogeneities", Med. Phys., Jan./Feb. 1993, vol. 20, No. 1, pp. 233-244.

Wong, J.K., et al., "Conservative Management of Osteoradionecrosis", Oral Surg. Oral Med. Pahol. Oral Pathol., Jul. 1997, vol. 84, No. 1, pp. 16-21.

Wong, J.W., (writing chair), "Role of Inhomogeneity Corrections in 3D Photon Treatment Planning", Int. J. Rad. Oncol. Biol. Physics. 1991, vol. 21, No. 1, pp. 59-69.

Wong, J.W., et al., "Development of a Second-Generation Fiber-Optic On-Line Image Verification System", Int. J. Radiat. Oncol. Biol. Phys., 1993, vol. 26, No. 2, pp. 311-320.

Wong, J.W., et al., "Effect of Small Inhomogeneities on Dose in a Cobalt-60 Beam", Med. Phys., Nov./Dec. 1981, vol. 8, No. 6, pp. 783-791.

Wong, J.W., et al., "On Methods of Inhomogeneity Corrections for Photon Transport", Med. Phys., Sep./Oct. 1990, vol. 17, No. 5, pp. 807-814.

Wong, J.W., et al., "On-Line Image Verification in Radiation Therapy: An Early USA Experience", Med. Prog. Through Technol., 1993, vol. 19, pp. 43-54.

Wong, J.W., et al., "On-Line Radiotherapy Imaging with an Array of Fiber-Optic Image Reducers", Int. J. Radiat. Oncol. Biol. Phys., Jun. 1990, vol. 18, No. 6, pp. 1477-1484.

Wong, J.W., et al., "Portal Dose Images. I: Quantitative Treatment Plan Verification", Int. J. Radiat. Oncol.Biol.Phys., Jun. 1990, vol. 18, No. 6, pp. 1455-1463.

Wong, J.W., et al., "Reconsideration of the Power-Law (Batho) Equation for Inhomogeneity Corrections", Med. Phys., Jul./Aug. 1982, vol. 9, No. 4, pp. 521-530.

Wong, J.W., et al., "Second Scatter Contribution to Dose in Cobalt-60 Beam" Med. Phys., Nov./Dec. 1981, vol. 8, No. 6, pp. 775-782.

Wong, J.W., et al., "The Cumulative Verification Image Analysis Tool for Offline Evaluation of Portal Images", Int. J. Radiat. Oncol.Biol. Phys., 1995, vol. 33, No. 5, pp. 1301-1310.

Wong, J.W., et al., "The Use of Active Breathing Control (ABC) to Reduce Margin for Breathing Motion", Int. J. Radiat. Oncol. Biol. Phys., 1999, vol. 44, No. 4, pp. 911-919.

Wong, J.W., et al., "Treatment Verifications and Patient Dose Estimations Using Portal Dose Imaging" Radiotherapy System Research (Japan). 1988; vol. 5, No. 3, pp. 213-225.

Wong, J.W., et al.; "A New Approach to CT Pixel-Based Photon Dose Calculations in Heterogeneous Media", Med. Phys., Mar./Apr. 1983, vol. 10, No. 2, pp. 199-208.

Wu, Y., et al., "Implementing multiple static field delivery for intensity modulated beams", Med. Phys., Nov. 2001, vol. 28, No. 11, pp. 2188-2197.

Xu, Xiaochao, et al., "A Tetrahedron Beam Computed Tomography Benchtop System With a Multiple Pixel Field Emission X-Ray Tube," Med. Phys., vol. 3, No. 10, 2001, pp. 5500-5508.

Yan, D., "Adapt Radiotherapy to Temporal Biological Targets Assessed Using Biological Images," publication source unknown, while the date of publication is unknown, it is believe that the article was publicly available before May 24, 2007, 3 pages.

Yan, D., "Image-Guided Adaptive Radiotherapy Model," AAPM, Mar. 10, 2006, pp. 1-15.

Yan, D., "Image-Guided/Adaptive Radiotherapy," Medical Radiology-Radiation Oncology, Volume: New Technologies in Radiation Oncology, Edited by W. Schlegel, T. Bortfeld and AL Grosu, Springer-Verlag, Berlin, Heidelberg, New York, Hong Kong, Sep. 8, 2005, ISBN 3-540-00321-5, pp. 317-332.

Yan, D., "Treatment Strategy for Daily Image Feedback Adaptive Radiotherapy," Proceeding, XIIIth International Conference on the Use of Computers in Radiotherapy, Heidelberg, Germany, 2000, pp. 518-520.

Yan, D., et al., "A Model to Accumulate Fractionated Dose in a Deforming Organ," Int. J. Radiation Oncology Biol. Phys., vol. 44, No. 3, 1999, pp. 665-675.

Yan, D., et al., "A New Model for "Accept or Reject" Strategies in Off-Line and On-Line Megavoltage Treatment Evaluation", Int. J. Radiat. Oncol. Biol. Phys., 1995, vol. 31, No. 4, pp. 943-952.

Yan, D., et al., "Adaptive Modification of Treatment Planning to Minimize the Deleterious Effects of Treatment Setup Errors," Int. J. Radiation Oncology Biol. Phys., vol. 37, No. 5, while the publication date is unknown, it is believed to have been published prior to 1999, pp. 1-27.

Yan, D., et al., "Adaptive Modification of Treatment Planning to Minimize the Deleterious effects of Treatment Setup Errors", Int. J. Radiat. Oncol. Biol. Phys., 1997, vol. 38, No. 1, pp. 197-206.

Yan, D., et al., "Adaptive Radiation Therapy," Phys. Med. Biol., vol. 42, 1997, pp. 123-132.

Yan, D., et al., "An Off-Line Strategy for Constructing a Patient-Specific Planning Target Volume For Image Guided Adaptive Radiotherapy of Prostate Cancer," Int. J. Radiation Oncology Biol. Phys., vol. 48, No. 1, 2000, pp. 289-302.

Yan, D., et al., "Computed Tomography Guided Management of Interfractional Patient Variation," Semin. Radiat. Oncol. vol. 15, 2005, pp. 168-179.

Yan, D., et al., "Organ/Patient Geometric Variation in External Beam Radiotherapy and Its Effect," Med. Phys., vol. 28, No. 4, Apr. 2001, pp. 593-602.

Yan, D., et al., "Strategies for Off-Line and On-Line Image Feedback Adaptive Radiotherapy," Editors: BK Paliwal, DE Herbert, JF Fowler, MP Mehta, Biological & Physical Basis of IMRT & Tomotherapy, AAPM Symposium Proceeding No. 12, 2002, pp. 139-150.

Yan, D., et al., "The influence of interpatient and intrapatient rectum variation on external beam treatment of prostate cancer", Int. J. Radiat. Oncol. Biol. Phys. 2001, vol. 51, No. 4, pp. 1111-1119.

Yan, D., et al., "The Use of Adaptive Radiation Therapy to Reduce Setup Error. A Prospective Clinical Study," Int. J. Radiation Oncology Biol. Phys., vol. 41, No. 3, 1998, pp. 715-720.

Yang, Y., et al., "Evaluation of On-Board kV Cone Beam CT (CBCT)-based Dose Calculation," Phys. Med. Biol., vol. 52, 2007, pp. 685-705.

Ying, X.G., et al., "Portal Dose Images. II: Patient Dose Estimation", Int. J. Radiat. Oncol. Biol. Phys., Jun. 1990, vol. 18, No. 6, pp. 1465-1475.

Yu, C.X., et al., "A Method for Implementing Dynamic Photon Beam Intensity Modulation Using Independent Jaws and a Multileaf Collimator", Phys. Med. Biol., 1995, vol. 40, pp. 769-787.

Yu, C.X., et al., "A Multiray Model for Calculating Electron Pencil Beam Distribution", Med. Phys., Sep./Oct. 1988, vol. 15, No. 5, pp. 662-671.

Yu, C.X., et al., "Photon Dose Calculation Incorporating Explicit Electron Transport", Med. Phys., Jul. 1995, vol. 22, No. 7, pp. 1157-1165.

(56) References Cited

OTHER PUBLICATIONS

Yu, C.X., et al., "Photon Dose Perturbations Due to Small Inhomogeneities", Med. Phys., Jan./Feb. 1987, vol. 14, No. 1, pp. 78-83.

Zeng, G.L., et al., "Image Reconstruction Algorithm for a Spect System with a Convergent Rotating Slat Collimator," IEEE Transactions on Nuclear Science, vol. 51, No. 1, 2004, pp. 142-148.

Zhang, J., et al., "A Multi-Beam X-Ray Imaging System Based on Carbon Nanotube Field Emitters," Medical Imaging 2006: Physics of Medical Imaging Proceedings of Spie, vol. 6142, 2006, eight pages.

Zhang, T., et al., "Automatic Delineation of Online Head and Neck CT Images: Towards Online Adaptive Radiotherapy," Int. J. of Radiation Oncology Biol. Phys., vol. 68, No. 2, 2007, pp. 522-530.

Zhang, Tiezhi, et al., "Tetrahedron Beam Computed Tomography (TBCT): A New Design of Volumetric CT System," Phys. Med. Biol., vol. 54, 2009, pp. 3365-3378.

International Search Report for PCT/US2007/008996, dated Mar. 4, 2008, three pages.

International Search Report for PCT/US2007/012607, dated Apr. 11, 2008, two pages.

\* cited by examiner kV + MV Portal Image

Reference DRR with BEV

Gantry=90

Gantry=135

Gantry=180

Gantry=270

INTENSITY MODULATED ARC THERAPY WITH CONTINUOUS COUCH ROTATION/SHIFT AND SIMULTANEOUS CONE BEAM IMAGING

Applicants claim, under 35 U.S.C. §119(e), the benefit of priority of the filing date of Jan. 5, 2010 of U.S. provisional patent application Ser. No. 61/335,314, filed on the aforementioned date, the entire contents of which are incorporated herein by reference.

BACKGROUND OF THE INVENTION

1. Field of the Invention

The present invention relates generally to systems and methods for treatment and delivery of therapeutic radiation and, in particular, relates to a system and method for additional continuous arc rotation/shift of a couch (C-ARC) in the volumetric modulated arc therapy (VMAT) delivery of therapeutic radiation, as well as simultaneous kV cone-beam imaging for real-time treatment verification and adaptation.

2. Discussion of Related Art

There are a number of known systems and method for treatment and delivery of therapeutic radiation. One of these is known as three-dimensional conformal radiation therapy (3D-CRT). 3D-CRT involves three-dimensional imaging, accurate radiation dose calculation, computer optimized treatment planning, and computer controlled treatment delivery. In particular, 3D-CRT uses computers and special imaging techniques such as CT, MR or PET scans to show the size, shape and location of a tumor as well as surrounding organs. The therapeutic radiation beams are then precisely tailored to the size and shape of the tumor with multileaf collimators or custom fabricated field-shaping blocks. The precise application of the therapeutic radiation beams results in nearby normal tissue receiving less radiation and so the normal tissue is able to heal more quickly after a therapeutic radiation session. The more normal tissue is shielded from receiving the therapeutic radiation allows for the amount of the radiation actually delivered to the tumor to be increased and so the chances of successfully treating the tumor increase. An example of 3D-CRT is described in the publication, Takahashi, S., "Conformation radiotherapy: rotation techniques as applied to radiography and radiotherapy of cancer," Acta Radiol 1965, Suppl. 242.

Another system and method for treatment planning and delivery of therapeutic radiation is known as intensity-modulated radiation therapy, or IMRT. IMRT is a specialized form of 3D-CRT that allows radiation to be modulated, thus more exactly shaped to fit the tumor. In particular, IMRT involves breaking up the therapeutic radiation beams into many "beamlets." The intensities of each beamlet are then adjusted individually. Such adjustment of intensities allows for the radiation received by healthy tissue near a tumor to be further reduced when compared with 3D-CRT. An example of IMRT is described in the publication, Brahme, A., et al., "Solution of an integral equation encountered in rotation therapy," Phys Med Biol Vol. 27, No. 10, 1982, pp. 1221-29.

A third system for treatment and delivery of therapeutic radiation is known as intensity modulated arc therapy (IMAT) and later volumetric-modulated arc therapy, also known as VMAT. VMAT addresses several of the disadvantages of IMRT, namely, increased treatment time by requiring a larger number of beam directions and the use of increased monitor units (MU). VMAT addresses these disadvantages by allowing continuous gantry/collimator rotation, leaf motion, and dose rate adjustment for treatment plan optimization where dose is delivered during a single gantry arc of up to 360 degrees. The VMAT technique is similar to tomotherapy in that a full 360 degree range of beam directions are available for optimization, but is fundamentally different from IMRT in that the entire dose volume is delivered in a single source rotation. An example of VMAT is described in: 1) Yu, C. X., "Intensity-modulated arc therapy with dynamic multileaf collimation: an alternative to tomotherapy," Phys Med Biol Vol. 40, 1995, pp. 1435-1449., 2) Yu, C. X., et al., "Clinical implementation of intensity-modulated arc therapy," Int J Radiat Oncol Biol Phys Vol. 53, 2002, pp. 453-463 and 3) Otto, K., "Volumetric modulated arc therapy: IMRT in a single gantry arc," Med Phys Vol. 35, 2008, pp. 310-317.

VMAT involves, in part, using multileaf collimator (MLC) leaf motion and dose rate adjustment to modulate beam output intensity. In addition, VMAT delivers the modulated beam intensity output by rotating the gantry and collimator of a linac through one or more complete or partial arcs with the therapeutic radiation continuously on so that treatment times are reduced. During rotation of the gantry, a number of parameters can be dynamically varied, such as: i) the MLC aperture shape, ii) the fluence-output rate ("dose rate"), iii) the gantry rotation speed and iv) the MLC orientation. Being able to vary the parameters i)-iv) allows VMAT to reduce the need to use as many arcs, delivering fewer monitor units (MU) in a shorter time while providing dosimetry comparable to IMRT. While VMAT can take advantage of the above-mentioned four available variable parameters, it must do so while respecting the physical constraints of the linac and MLC—such as the maximum gantry speed, maximum leaf speed, the MLC orientation constraints and the available subdivisions of fluence-output rate.

Without dynamically controlling all machine parameters, specifically the orientations between machine and patient, during treatment delivery, current VMAT technology is limited for certain treatment sites. In the case of breast cancer treatment, it has been shown that VMAT applied to treat left-sided breast cancers with internal mammary node irradiation resulted in an increase in the volume of lungs, heart and contralateral breast receiving low dose (5 Gy) irradiation compared to modified wide tangents. By definition, due to its configuration, VMAT used for breast irradiation contains beams directed towards the heart, lungs, and contralateral breast.

Another disadvantage of VMAT systems is that they do not integrate simultaneous kV imaging. Accordingly, such VMAT systems are not capable of real-time treatment verification

SUMMARY

One aspect of the present invention regards a system for radiotherapy that includes a couch upon which a patient being treated by the system sits, the couch having continuous arc rotation and shift for delivery accelerated irradiation to the patient.

A second aspect of the present invention regards a radiation therapy system that includes a radiation source that moves about an object and directs a beam of radiation towards the object. The radiation therapy system further includes 1) a multi-leaf collimator having a plurality of movable leafs that define an aperture through which the beam is directed from the radiation source to the object and 2) a table upon which the object is positioned, the table being translationally and rotationally movable. The radiation therapy system further includes a computer in communication with the radiation source, the multi-leaf collimator and the table, wherein the computer simultaneously controls one or more of the following parameters of the radiation source, the multi-leaf collimator and the table: table motion, radiation source motion, fluence output rate, multi-leaf collimator orientation and shape of the aperture.

A third aspect of the present invention regards a method of providing radiation that includes directing a beam of radiation towards an object, defining an aperture through which the beam is directed to the object and positioning a table upon which the object lies. The method further including simultaneously controlling one or more of the following parameters: table motion, beam motion, fluence output rate, aperture orientation and shape of the aperture.

A fourth aspect of the present invention regards a radiation therapy system that includes a radiation source that moves about an object and directs a beam of therapeutic radiation towards the object and an imaging source that moves about the object and directs a beam of imaging radiation towards the object. The system further includes a table upon which the object is positioned, the table being translationally and rotationally movable. The system also includes 1) a first imager for receiving radiation passing through the object that was generated by the therapeutic radiation source and for forming a first image information therefrom and 2) a second imager for receiving radiation passing through the object that was generated by the imaging source and for forming a second image information therefrom, wherein the first image information and the second image information are formed simultaneously. The system additionally includes a computer in communication with the radiation source, the table, the first imager and the second imager, wherein the computer simultaneously controls motion of the table and one or more of the following parameters of the radiation source in a real-time manner based on the first image information and the second image information: radiation source motion and fluence output rate.

A fifth aspect of the present invention regards a method of providing radiation that includes directing a beam of therapeutic radiation towards an object and directing a beam of imaging radiation towards the object. The method includes positioning an object upon a table that is translationally and rotationally movable. The method also includes forming first image information of the object based on the beam of therapeutic radiation passing through the object and forming second image information of the object based on the beam of imaging radiation passing through the object, wherein the first image information and the second image information are formed simultaneously. The method further including simultaneously controlling movement of the table and one or more of the following parameters of the beam of therapeutic radiation in a real-time manner based on the first image information and the second image information: beam of therapeutic radiation motion and fluence output rate.

One or more aspects of the present invention provide the advantage of prescribing fewer monitor units and using fewer control points.

One or more aspects of the present invention provide for reducing irradiation in breast treatment to all OARs: breasts, lungs, and heart without compromising target coverage.

One or more aspects of the present invention decrease the risk of toxicity and secondary malignancy.

DESCRIPTION OF THE PREFERRED EMBODIMENTS

Figure 1:
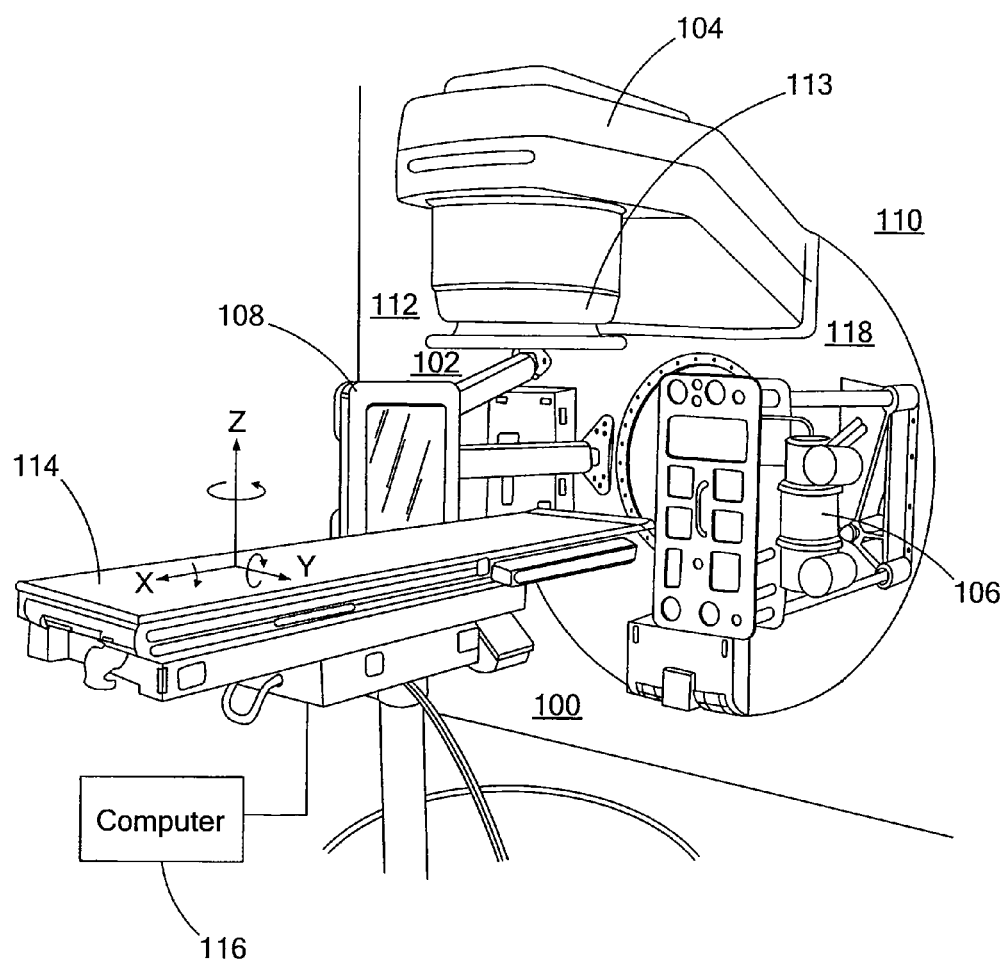
FIG. 1 shows an embodiment of a radiation therapy system that can perform C-ARC therapy in accordance with the present invention.

As shown in FIG. 1, there is shown a radiation therapy system 100 that can include an imaging system, such as a cone beam computed tomography system 102, and a therapeutic radiation source, such as medical linear source or accelerator 104. The computed tomography system 102 includes an x-ray source 106 and a flat panel imager 108 mounted on gantry 110. The details of the computed tomography system 102 is described in U.S. Pat. Nos. 6,842,502 and 7,471,765, the entire disclosures of each of which are incorporated herein by reference. Of course, other types of imaging systems, such as C-arm support cone beam systems and proton imaging systems, can be used without departing from the spirit of the present invention.

The system 102 is retrofitted onto an existing or new radiation therapy system 112 that includes a separate radiation therapy source, such as the medical linear source 104, which operates at a power level to allow for treatment of a target volume in an object, such as a human patient. The medical linear source 104 generates a beam of x-rays or particles, such as photons, protons or electrons, which have an energy ranging from 4 MeV to 25 MeV. Indeed, the medical linear source 104 could be replaced with other radiation sources used for therapeutic treatment of patients without departing from the spirit of the present invention. The radiation therapy system 112 further includes a multi-leaf collimator (MLC) 113 that is movable as a unit and includes leafs that are movable so as to define an aperture for the therapy beam to pass through on to the patient. The radiation therapy system 112 may also include an imager (not shown) that is aligned with the medical linear source 104 with the patient interposed therebetween.

For support of the patient and for aiding in the application of the therapeutic radiation beam, a computer-controlled treatment table 114 is provided. The table 114 is controlled by a computer, such as computer 116 schematically shown in FIG. 1. The table 114 allows translation of the patient in the x, y, and z directions as well as rotation about the x, y and z axes. Furthermore, the treatment table 114 is preferably constructed of radio-translucent material so as not to interfere significantly with the acquisition of computed tomography images. The table 114 can have many forms such as disclosed in U.S. Pat. Nos. 6,842,502 and 7,471,765 and U.S. Patent Application Publication No. US2010-0119032A1, the entire contents of each of which are incorporated herein by reference.

The system 100 of FIG. 1 is controlled by computer 116 so as to perform C-ARC therapeutic radiation treatment plans in accordance with the present invention. In particular, C-ARC, like VMAT, involves combining a modulated beam aperture and dose rate with rotational delivery. In contrast to VMAT, C-ARC introduces an alternative modality of delivering rotation. In particular, the table or couch 114 moves via translation and/or rotation so as to control therapeutic radiation delivery to the area of interest. Note that the translation of the table 114 can be in one or more of the x, y and z directions shown in FIG. 1. In addition, the rotation of the table 114 can be in about one or more of the x, y and z directions. During rotation of the table 114, the ring 118 of gantry 110 can also rotate simultaneously for certain treatment sites, such as the brain.

Figure 2:
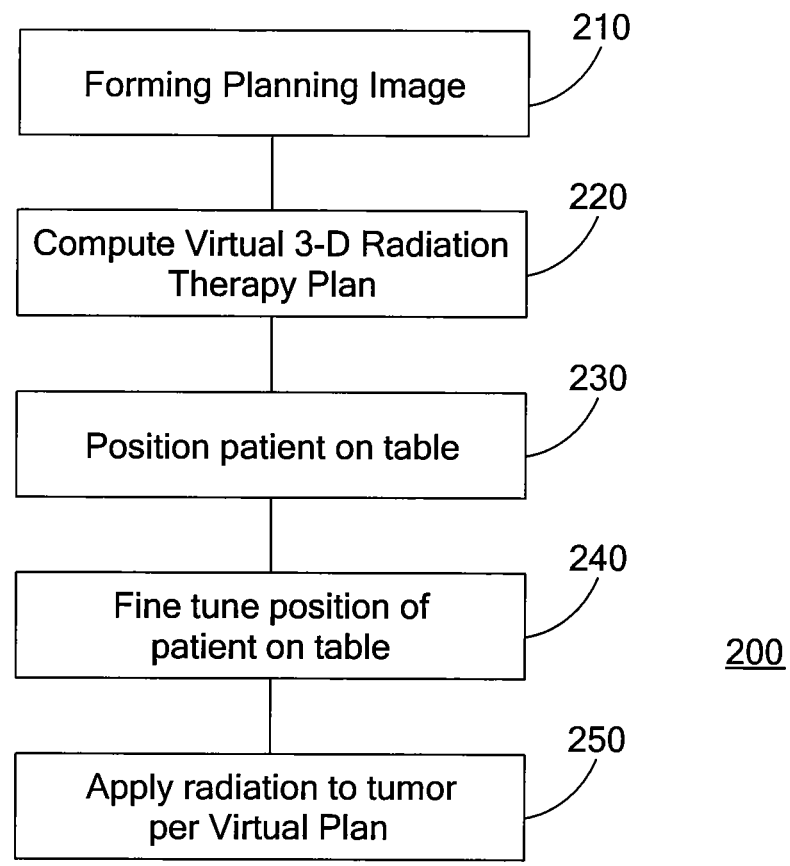
FIG. 2 shows a flow chart of a possible process for operation of the radiation therapy system of FIG. 1 in accordance with the present invention.

While the table 114 is moving, the aperture shape and the orientation of the MLC 113 can be dynamically varied. In addition, the fluence-output rate ("dose rate") and gantry rotation speed and consequently speed of rotation of the radiation source 104 can be varied. Control of the table motion, the gantry motion, fluence-output rate, MLC orientation and shape of the MLC is performed by computer 116. The software used to control the computer 116 can be similar to software used in VMAT, wherein the software for C-ARC is such that clinically acceptable dosimetry is generated while avoiding any collision between the table 114, gantry 110 and its attachments, and the patient. With the above description of the system 100 in mind, a possible process for operation of the system 100 is described herein with respect to the flow chart of FIG. 2. In particular, a process 200 is schematically shown that involves first forming a computed tomography or other three dimensional planning image of an area of the patient that is known to contain an object of interest, such as a tumor, for treatment per process 210. The planning image can be performed off-site or by using the computed tomography system 102 on-site. The three-dimensional information of the image of the general area of the tumor is then fed to computer 116 or another computer to compute a virtual three-dimensional radiation therapy plan per process 220 for varying table motion, gantry motion, fluence output rate, MLC orientation and shape of the MLC in order to apply a desired therapy dose to the tumor while reducing dosage to healthy tissue.

After the virtual plan is computed, the patient can now be treated with radiation in accordance with the plan. With that said, it should be kept in mind that the virtual plan assumes that the tumor will be positioned at the same spatial position when it was imaged per process 210. When the patient is placed on the table 114 per process 230, the spatial position of the tumor can be fine tuned per process 240 to be the same when it was imaged per process 210 in one of two manners. One manner for fine tuning the spatial position is to have the technician reposition the patient until he or she visualizes that a skin marker on the patient is in the same position that it was when the image was taken per process 210. A second manner of fine tuning is to take a three-dimensional image of the tumor using computed tomography system 102 and adjust the position of the patient so that the tumor shown in the fine tuning image will be repositioned to coincide with the position of the tumor determined per process 210. Once the patient has been repositioned per process 240, the virtual plan of process 220 is then applied to the tumor per process 250.

Note that besides the fine tuning process mentioned previously, the treatment using the C-ARC plan can be performed in a real-time manner as described in U.S. Pat. Nos. 6,842,502 and 7,471,765, wherein real-time imaging of the tumor is performed during the radiation treatment and the real-time images of the tumor are used by computer 116 to control the table motion, the gantry motion, fluence output rate, MLC orientation and shape of the MLC.

Figure 3:
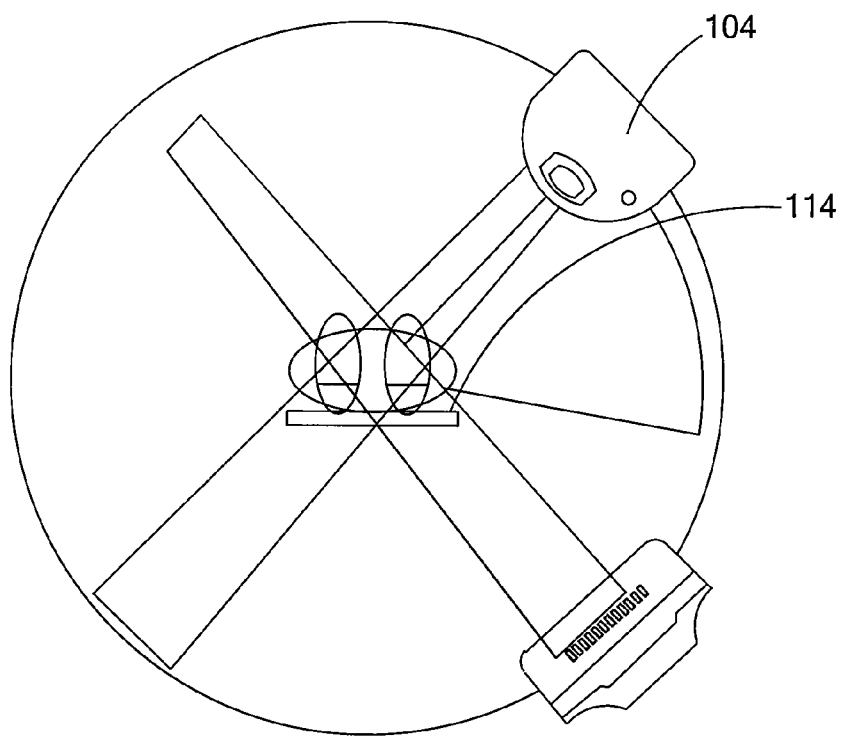
FIG. 3 schematically shows a system for simultaneous kV/MV imaging in accordance with the present invention.
Figure 5A:
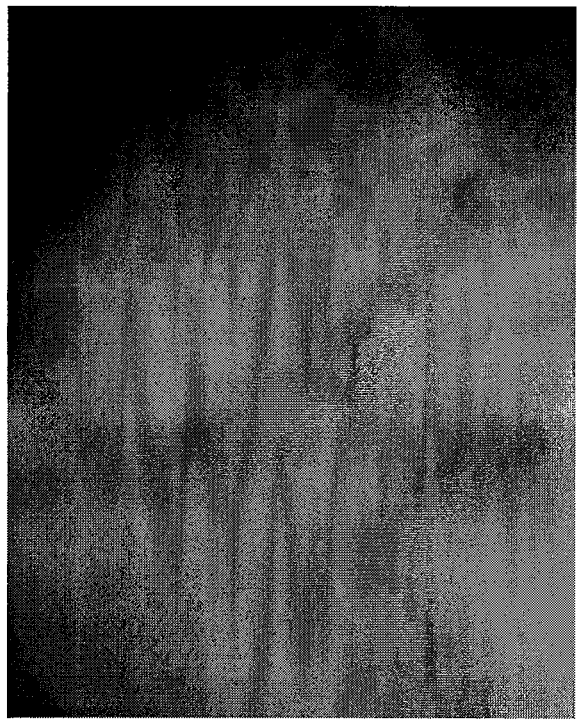
FIGS. 5A-D show kV and MV portal images at gantry positions of 90°, 135°, 180° and 270°, respectively, for an Stereotactic Radiosurgery treatment.
Figure 4A:
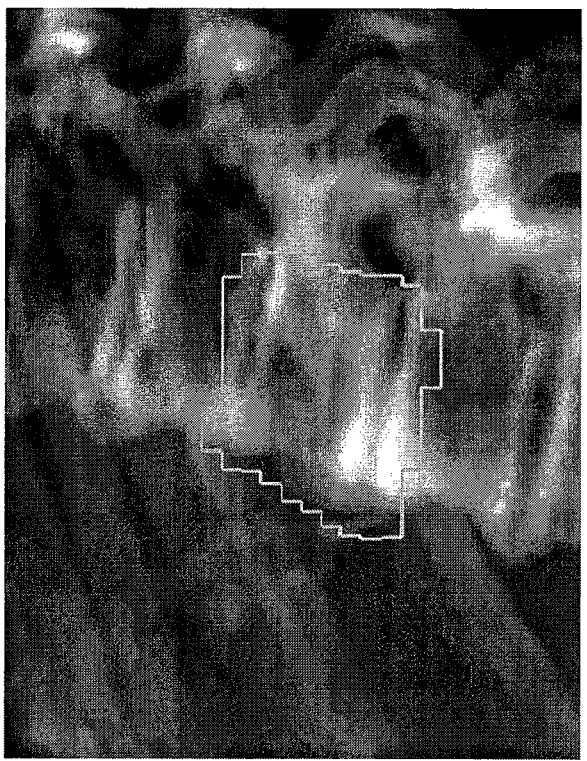
FIGS. 4A-D show reference digitally reconstructed radiographic (DRR) with beams eye view (BEV) images at gantry positions of 90°, 135°, 180° and 270°, respectively, for an Stereotactic Radiosurgery (SRS) treatment.
Figure 4B:
Figure 5B:
Figure 5C:
Figure 4C:
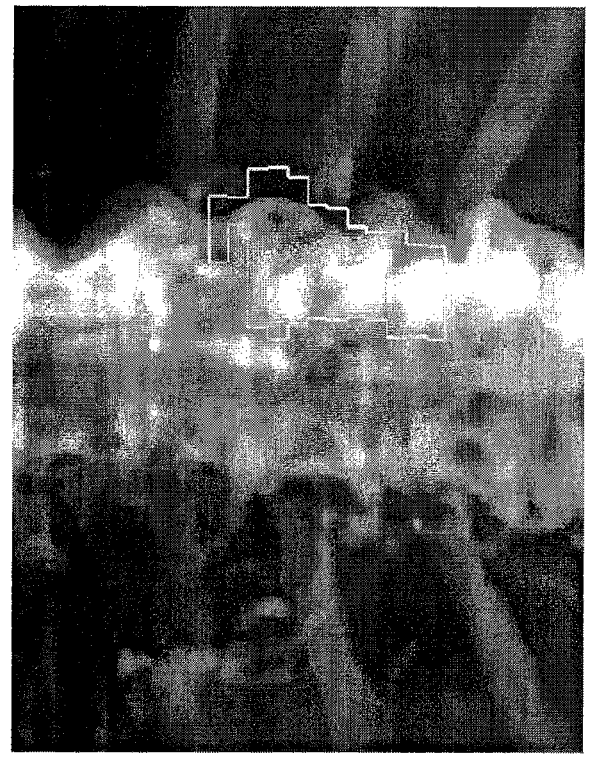
Figure 5D:
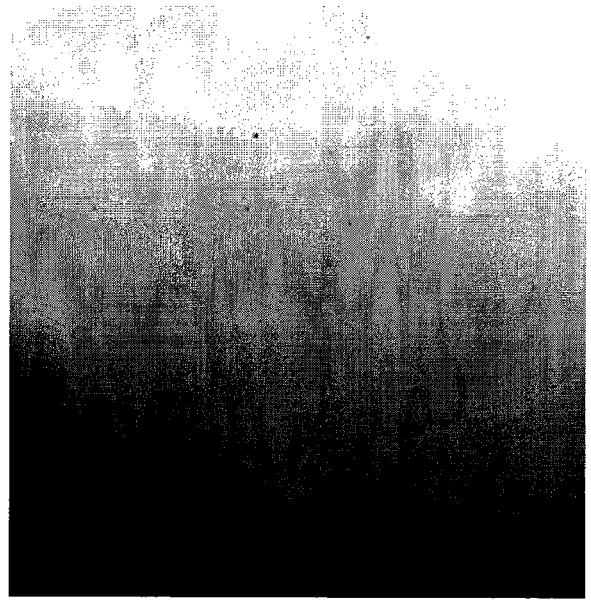
Figure 4D:

An example of the above described real-time C-ARC treatment is schematically shown in FIG. 3. In particular, a kV cone beam is directed through the patient on table 114 and a three dimensional real time image is generated on a flat panel imager 108. In addition, an MV portal imager 120 is also simultaneously used to generate a real-time two-dimensional image of the patient based on the therapeutic radiation emitted by source 104 (not shown) that is positioned opposite the imager 120. Such simultaneous real-time imaging by both kV cone beam projection imaging and MV portal imaging during therapeutic radiation delivery is made possible by taking advantage of the rotation features of VMAT and C-ARC in beam patient orientation. The projection images of MV portal imaging and kV cone beam projection imaging can be processed for 2D and 3D verification images, respectively, to monitor patient/anatomy position motion/variation in real-time during the therapeutic radiation treatment.

Examples of kV and MV portal images formed by the kV cone beam and MV imagers described above and at various gantry rotational positions are shown in FIGS. 5A-D, wherein an area of a spine is being treated. Corresponding images of reference digitally reconstructed radiographic with beam's eye view are shown in FIGS. 4A-D. (it represents the object within the beam direction and aperture)

With the above description of the C-ARC treatment plan, a comparison with other known treatment plans illustrates the advantages of the present invention. In the case of treatment of tumors in the breast via accelerated partial breast irradiation (APBI), the gantry 110 remains stationary at tangent angles while the table 114 rotates through one medial and one lateral arc, wherein the medial and lateral arcs are defined with respect to the orientation of the breast of the patient.

Figures 6A, 6B, 6C, 7A, 7B, 7C:
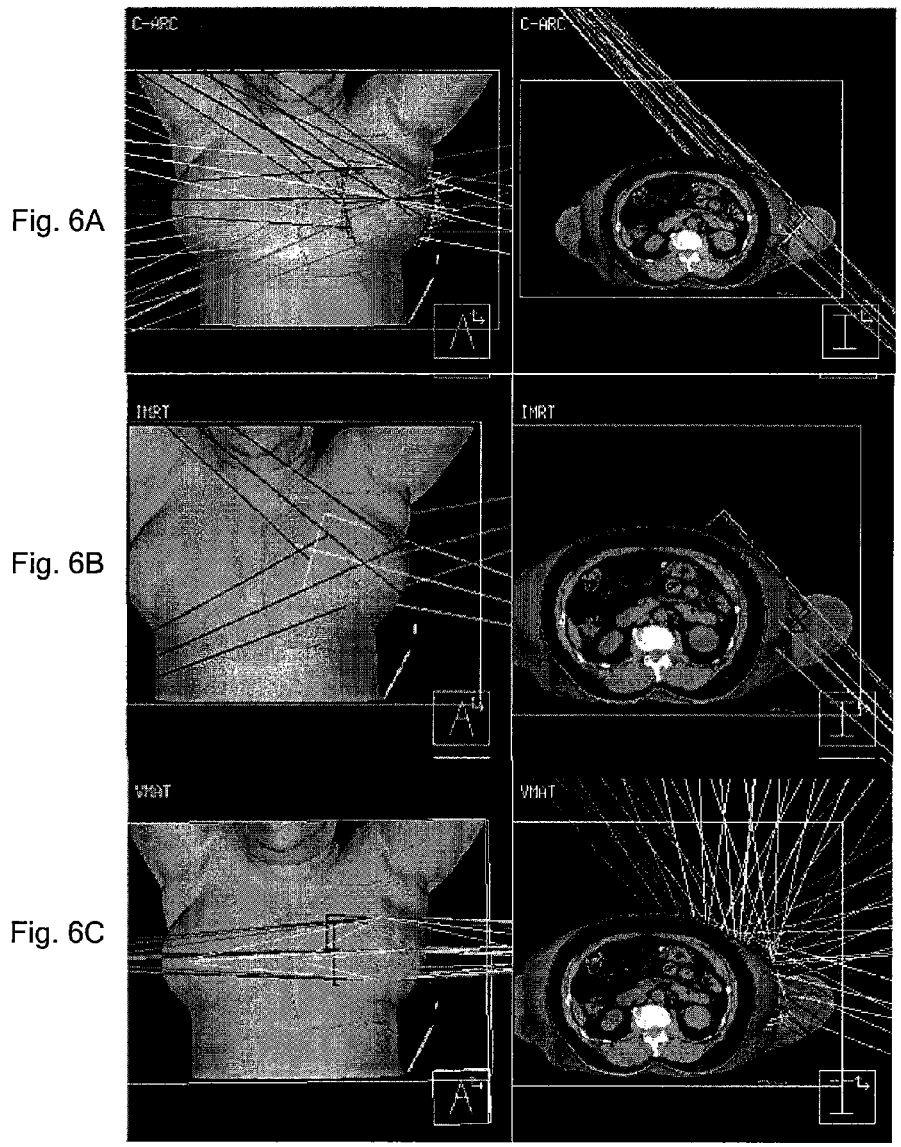
FIG. 6A shows an external view of a possible beam arrangement for breast tumor treatment in accordance with the present invention.
FIGS. 6B-C show external views of beam arrangements for known breast tumor treatment plans.
FIG. 7A shows an internal view of the beam arrangement for breast tumor treatment of FIG. 6A.
FIGS. 7B-C show internal views of the beam arrangements for breast tumor treatment of FIGS. 6B-C, respectively.

In the case of when the breast in question has been previously treated by a 3D-CRT plan, the beam arrangement of the 3D-CRT plan can be used to guide C-ARC planning, as it is deemed to have provided clinically acceptable dosimetry while avoiding any collision between the table, gantry, and the patient. The table positions from the 3D-CRT plan are taken as the limits of the table arcs. Similarly, the gantry position for each arc is chosen to be the same as that in the 3D-CRT plan. Optimization and dose calculation is done with control points positioned at 10° intervals along the arcs. Such breast treatment Maintains the benefits of the standard tangent beam arrangement of APBI treated with 3D-CRT. C-ARC is a natural extension of the innovation of VMAT to the realm of breast radiotherapy, in which the standard tangent beam geometry minimizes dose outside the target. This is shown in FIGS. 6A and 7A where radiations beams using C-ARC are directed mostly to the breast and little radiation affects healthy organs, such as the heart and lungs. In contrast, APBI when applied with IMRT and VMAT can lead to beams being directed to health tissue as shown in FIGS. 6B-C and 7B-C.

In the comparison to follow, it regards patients previously treated with APBI via 3D-CRT and three additional and subsequent plans were generated for each patient: 1) a C-ARC plan, 2) an IMRT plan, and 3) a VMAT plan. The DVH parameters used for evaluation were taken largely from the normal tissue constraints of the NSABP-B39/RTOG 0413 protocol for breast therapy and are listed in Table 1 below:

($p=0.011$). A non-significant trend ($p=0.05$) emerged of the C-ARC plans delivering a lower Dmax to the contralateral breast.

In addition to reducing the dose to the ipsilateral breast, C-ARC plans decrease dose to the lung and heart. C-ARC and IMRT provided the greatest reductions in ipsilateral lung irradiation as measured by V5 Gy due to their lack of en face geometry. C-ARC and IMRT plans also produced significant reductions in low dose irradiation of the heart.

TABLE 1

Normal tissue dose constraints of the NSABP B-39/RTOG 0413 protocol and plan comparison parameters, mean values and range, for 3D-CRT, IMRT, C-ARC, and VMAT plans

| | NSABP B-39/ RTOG 0413 Normal Tissue Dose Constraints (1) | 3D-CRT | C-ARC | p | IMRT | p | VMAT | p |
|---|---|---|---|---|---|---|---|---|
| Normal breast V50% | <60% | 50.5% (39.5-61.1) | 42.7% | <0.001 | 42.8% (35.1-49.2) | <0.001 | 42.6% (34.6-50.6) | 0.001 (33.7-52.7) |
| Normal breast V100% | <35% | 20.2% (11.6-31.3) | 17.0% | <0.001 | 16.6% (14.4-24.5) | <0.001 | 15.8% (10.2-25.9) | <0.001 (8.3-24.5) |
| Ipsilateral lung V30% | <15% | 6.1% (0.3-10.0) | 3.6% | 0.004 | 3.5% (0.1-8.5) | 0.003 | 3.7% (0.2-8.2) | 0.002 (0.0-8.1) |
| Ipsilateral lung V5Gy | n/a | 11.2% (1.2-17.6) | 7.8% | 0.001 | 7.7% (0.9-12.9) | 0.005 | 10.4% (1.0-13.0) | 0.381 (2.2-17.7) |
| Heart V5% | <5% for right-sided lesions <40% for left-sided lesions | 6.8% (0.0-43.0) | 5.5% | 0.018 | 5.7% (0.0-39.1) | 0.018 | 7.7% (0.0-38.6) | 1 (0.0-39.5) |
| Contralateral breast Dmax | <3% | 374.80 (58.10-2451.20) | 260.97 | 0.006 | 198.25 (56.30-1841.60) | 0.002 | 288.24 (54.5-1364.00) | 0.42 (86.30-1529.20) |
| Monitor Units | n/a | 827.21 (607.45-1084.30) | 488.31 | <0.001 | 691.33 (448.40-525.90) | 0.013 | 546.44 (555.00-928.30) | <0.001 (484.40-667.00) |
| Control Points | n/a | 4 | | | 9-14 | | 23-25 | 18-20 |

Figure 8B:
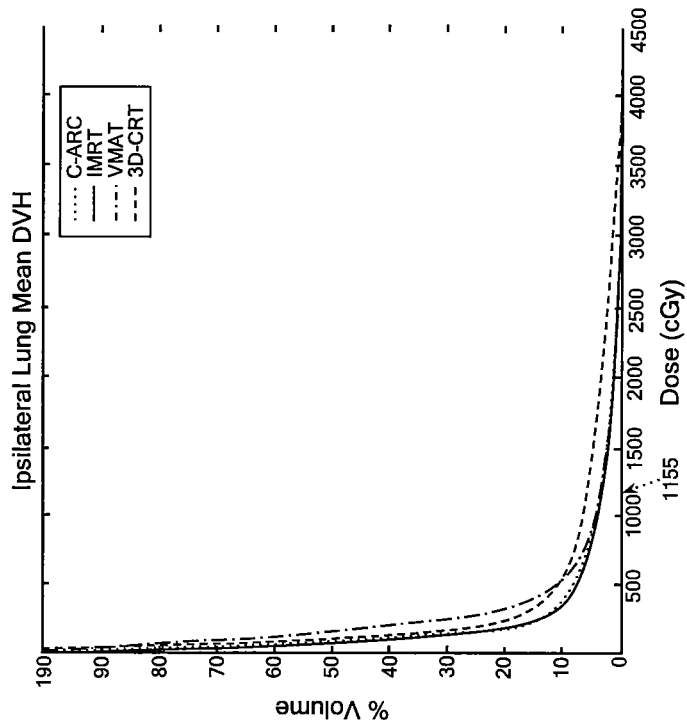
FIG. 8B shows for the Ipsilateral Lung % Volume v. Dose plots of various known treatment plans when compared with a treatment plan in accordance with the present invention.
Figure 8A:
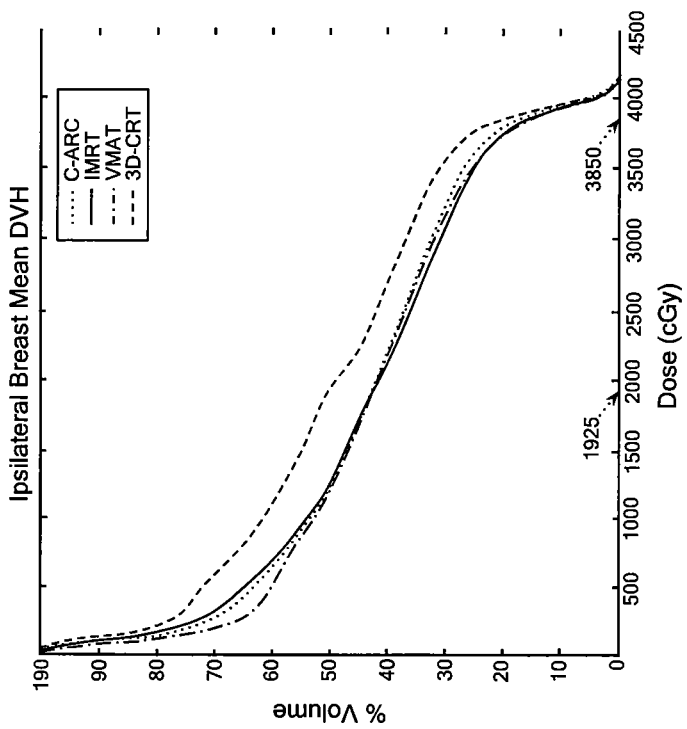
FIG. 8A shows the Ipsilateral Breast % Volume v. Dose plots of various known treatment plans when compared with a treatment plan in accordance with the present invention.

Table 1 above lists the mean values for the normal tissue doses of the C-ARC, IMRT, and VMAT plans, all of which are compared to the original 3D-CRT plan. All three treatment planning modalities significantly decrease the volume of normal ipsilateral breast tissue V50%, reducing this value by 7.8% on average (See FIG. 8A). As shown, all three plans significantly decrease the ipsilateral lung V30%, but only the C-ARC and IMRT plans do so for the V5 Gy (See FIG. 8B). There are no significant reductions in the contralateral lung V5%. Four VMAT plans generate an unavoidably high Dmax in the contralateral breast that exceeds both the 3D-CRT plan and the normal tissue dose constraints outlined in the NSABP B-39/RTOG 0413 protocol (Table 1). None of the IMRT and C-ARC plans produce such violations. The C-ARC, IMRT, and VMAT plans all significantly reduce the number of monitor units compared with 3D-CRT, with the C-ARC plans prescribing the lowest mean number of MU (mean decrease: IMRT 136 MU, $p=0.013$, VMAT 281 MU, $p<0.001$, C-ARC 339 MU, $p<0.001$).

Figures 9A, 9B:
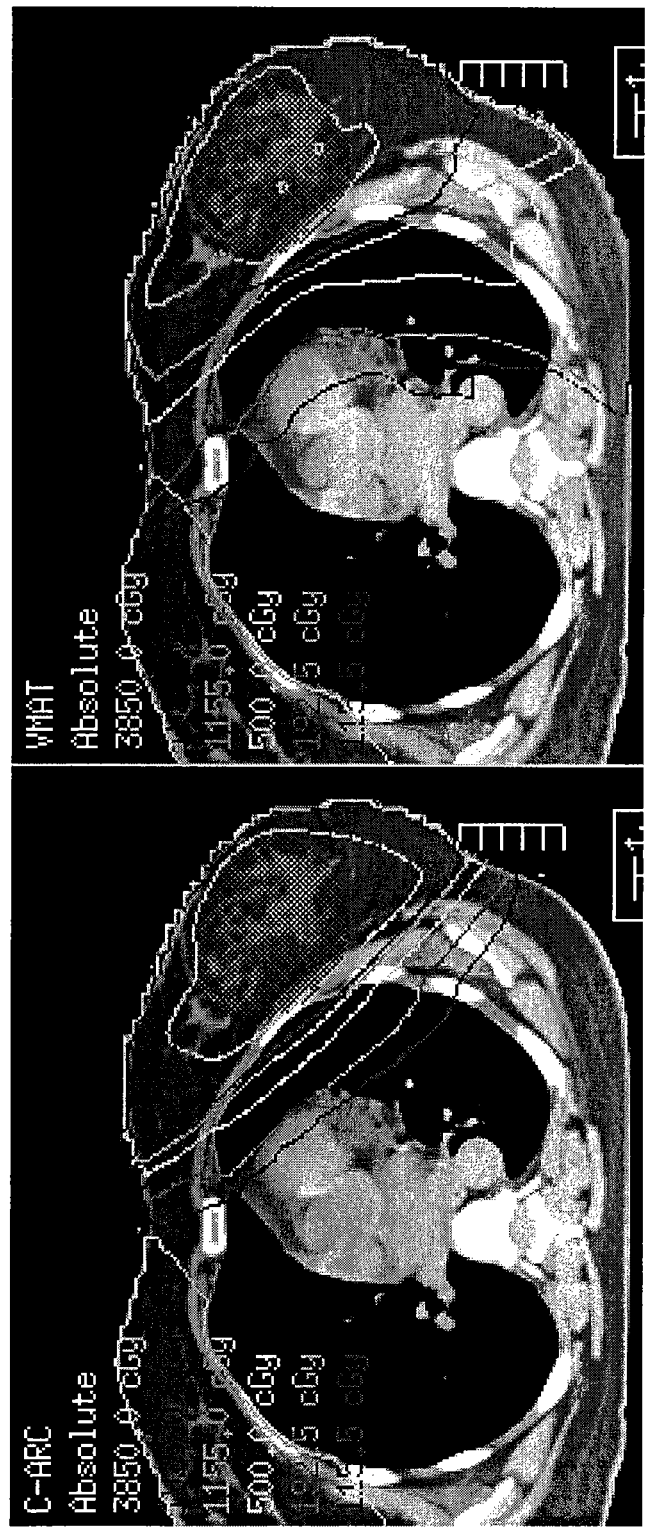
FIG. 9A shows representative axial dose distributions for a treatment plan for breast tumors in accordance with the present invention.
FIG. 9B shows representative axial dose distributions for a VMAT treatment plan.

C-ARC and VMAT plans are also compared. These two planning modalities produce comparable reductions in the volume of ipsilateral breast receiving 50% and 100% of the prescribed dose, as well as the ipsilateral lung receiving 30% of the prescribed dose. However, VMAT plans result in significantly larger ipsilateral lung volumes receiving 5 Gy (10.4% vs. 7.8%, $p=0.008$) and heart volumes receiving 192.5 cGy (7.7% vs. 5.5%, $p=0.021$). FIGS. 9A-B show representative axial dose distributions for C-ARC and VMAT, respectively. As well, C-ARC plans prescribed a significantly lower number of monitor units compared to VMAT plans Due to a lack of wedges, the C-ARC, IMRT, and VMAT plans all reduced the number of monitor units prescribed in comparison to the 3D-CRT plans, with C-ARC plans providing the greatest reduction. C-ARC plans also used the smallest number of control points, thereby minimizing leakage radiation.

As shown in Table 1, C-ARC plans produce a significant reduction in ipsilateral breast irradiation without increasing dose to the lungs, heart, and contralateral breast. VMAT plans are also able to reduce radiation dose to the ipsilateral breast, but this can come more often at the expense of increased dose elsewhere.

A natural extension of VMAT, C-ARC will allow for treatment with improved conformality, decreased delivery of monitor units, and anticipated shorter treatment times. The complexity of C-ARC is not significantly greater than that of existing arc therapy from the point of view of the treatment planner and operator. In order for this innovation to take place it will be necessary to link couch rotation control to dose rate and multileaf collimator motion. Minor modification of VMAT planning software will also be required to incorporate couch arcs.

In the case of APBI C-ARC therapy, the gantry 110 is stationary while the table 114 moves. There are instances where C-ARC therapy can involve simultaneous movement of the table 114 and the gantry 110. An example of this is when partial brain radiation therapy is employed. Movement of the table 114 and gantry 110 allows for the amount of therapeutic radiation applied to the healthy areas involving the optic chiasm, optic nerve and brain stem. Indeed, when compared with IMRT, C-ARC therapy employs reduced mean and maximum dosages for the optic chlasm, optic nerve and brain stem when compared with IMRT From the foregoing description, one skilled in the art can readily ascertain the essential characteristics of this invention, and without departing from the spirit and scope thereof, can make various changes and/or modifications of the invention to adapt it to various usages and conditions.

We claim:

1. A system for radiotherapy comprising:
a couch having a top lateral surface upon which a patient being treated by the system is positioned, the couch having continuous arc rotation for delivery of accelerated irradiation to the patient;
wherein the couch is rotatable at least about a z-axis orthogonally extending through a substantially central portion of the lateral surface; and
wherein delivery of the accelerated irradiation is performed during at least a portion of the movement.

2. The system of claim 1, wherein the couch has continuous translation for delivery of accelerated irradiation to the patient.

3. The system of claim 1, wherein the accelerated irradiation comprises particles.

4. The system of claim 3, wherein particles are selected from the group consisting of electrons and protons.

5. The system of claim 1, further comprising an imaging system to generate image information that identifies an object of interest within the patient to be treated by the accelerated irradiation.

6. The system of claim 5, wherein the image information is formed in a real-time manner during the continuous rotation of the couch and such image information is used to control continuous rotation of the couch in a real-time manner.

7. The system of claim 2, further comprising an imaging system to generate image information that identifies an object of interest within the patient to be treated by the accelerated irradiation.

8. The system of claim 7, wherein the image information is formed in a real-time manner during the continuous rotation and translation of the couch and such image information is used to control continuous rotation and translation of the couch in a real-time manner.

9. The system of claim 1, wherein the continuous rotation of the couch is based on image information of the patient generated prior to the patient being placed on the couch.

10. The system of claim 2, wherein the continuous rotation and continuous translation of the couch is based on image information of the patient generated prior to the patient being placed on the couch.

11. A radiation therapy system comprising:
a radiation source that moves about an object and directs a beam of radiation towards said object;
a multi-leaf collimator comprising a plurality of movable leafs that define an aperture through which said beam is directed from said radiation source to said object;
a table upon which said object is positioned, said table being translationally and rotationally movable, wherein the table is rotatable at least about a z-axis orthogonally extending through a substantially central portion of the lateral surface; and
a computer in communication with said radiation source, said multi-leaf collimator and said table, wherein said computer simultaneously controls one or more of the following parameters of said radiation source, said multi-leaf collimator and said table: table motion, radiation source motion, fluence output rate, multi-leaf collimator orientation and shape of said aperture;
wherein the computer is configured to cause delivery of the radiation during at least a portion of the movement of the table.

12. The system of claim 11, wherein said beam comprises photons.

13. The system of claim 11, wherein said beam comprises particles.

14. The system of claim 13, wherein said particles are selected from the group consisting of electrons and protons.

15. The system of claim 11, wherein said object is a tumor.

16. The system of claim 11, further comprising an imaging system to generate image information that identifies an orientation of said object.

17. The system of claim 16, wherein said image information is formed in a real-time manner during rotational and translational movement of said table and such image information is used to simultaneously control one or more of the following parameters in a real time manner: table motion, table motion speed, radiation source motion, fluence output rate, multi-leaf collimator orientation and shape of said aperture.

18. The system of claim 16, wherein simultaneous control of one or more of the following parameters table motion, radiation source motion, fluence output rate, multi-leaf collimator orientation and shape of said aperture is performed based on image information of said object generated prior to a patient containing said object being positioned on said table.

19. A method of providing radiation comprising:
directing a beam of radiation towards an object;
defining an aperture through which said beam is directed to said object;
positioning a table having a top lateral surface upon which said object lies;
rotating said table at least about a z-axis orthogonally extending through a substantially central portion of said lateral surface, wherein the beam of radiation is delivered to the object at least during a portion of the rotating; and
simultaneously controlling one or more of the following parameters: table motion, beam motion, fluence output rate, aperture orientation and shape of said aperture.

20. The method of claim 19, wherein said beam of radiation comprises photons.

21. The method of claim 19, wherein said beam of radiation comprises particles.

22. The method of claim 21, wherein said particles are selected from the group consisting of electrons and protons.

23. The method of claim 19, wherein said object is a tumor.

24. The method of claim 19, further comprising generating image information that identifies an orientation of said object.

25. The method of claim 24, wherein said image information is formed in a real-time manner during rotational and translational movement of said table and such image information is used to simultaneously control one or more of the following parameters in a real time manner: table motion, beam motion, fluence output rate, aperture orientation and shape of said aperture.

26. The method of claim 19, wherein said generating image information is performed prior to a patient containing said object being positioned on said table, and wherein said simultaneously controlling is based on said image information.

27. A radiation therapy system comprising:
a radiation source that moves about an object and directs a beam of therapeutic radiation towards said object;

an imaging source that moves about said object and directs a beam of imaging radiation towards said object;

a table having a top lateral surface upon which said object is positioned, said table being translationally and rotationally movable, the table being rotatable at least about a z-axis orthogonally extending through a substantially central portion of the lateral surface;

a first imager for receiving radiation passing through said object that was generated by said therapeutic radiation source and for forming first image information therefrom;

a second imager for receiving radiation passing through said object that was generated by said imaging source and for forming second image information therefrom, wherein said first image information and said second image information are formed simultaneously; and a computer in communication with said radiation source, said table, said first imager and said second imager, wherein said computer simultaneously controls motion of said table and one or more of the following parameters of said radiation source in a real-time manner based on said first image information and said second image information: radiation source motion and fluence output rate, such that delivery of radiation to said object is performed during movement of the table.

28. The system of claim 27, further comprising a multi-leaf collimator comprising a plurality of movable leaves that define an aperture through which said beam is directed from said radiation source to said object; and wherein said computer controls multi-leaf collimator orientation and shape of said aperture in a real-time manner based on said first image information and said second image information.

29. The system of claim 28, wherein said beam of therapeutic radiation comprises photons and said beam of imaging radiation comprises kV x-rays.

30. The system of claim 28, wherein said beam of therapeutic radiation comprises particles and said beam of imaging radiation comprises kV x-rays.

31. The system of claim 30, wherein said particles are selected from the group consisting of electrons and protons.

32. The system of claim 27, wherein said object is a tumor.

33. A method of providing radiation comprising:
directing a beam of therapeutic radiation towards an object;
directing a beam of imaging radiation towards said object;
positioning an object upon a top lateral surface of a table, the table being translationally movable and rotatable at least about a z-axis orthogonally extending through a substantially central portion of the lateral surface;
forming first image information of said object based on said beam of therapeutic radiation passing through said object;
forming second image information of said object based on said beam of imaging radiation passing through said object, wherein said first image information and said second image information are formed simultaneously; and
simultaneously controlling movement of said table and one or more of the following parameters of said beam of therapeutic radiation in a real-time manner based on said first image information and said second image information: beam of therapeutic radiation motion and fluence output rate.

34. The method of claim 33, wherein said simultaneously controlling further comprises controlling the shape of said beam of therapeutic radiation.

35. The method of claim 33, wherein said beam of therapeutic radiation comprises photons and said beam of imaging radiation comprises kV x-rays.

36. The method of claim 33, wherein said beam of therapeutic radiation comprises particles and said beam of imaging radiation comprises kV x-rays.

37. The method of claim 36, wherein said particles are selected from the group consisting of electrons and protons.

38. The method of claim 33, wherein said object is a tumor.

* * * * *